ic Patent [19] [11] Patent Number: 4,731,362
Hamashima et al. [45] Date of Patent: Mar. 15, 1988

[54] ALKYLCARBAMOYLOXYMETHYL-CEPHEM COMPOUNDS

[75] Inventors: Yoshio Hamashima, Kyoto; Teruji Tsuji; Tetsuo Okada, both of Osaka; Kyoji Minami, Nara; Hiroyuki Ishitobi, Osaka; Koji Ishikura, Nara, all of Japan

[73] Assignee: Shionogi & Co., Ltd., Osaka, Japan

[21] Appl. No.: 888,435

[22] Filed: Jul. 23, 1986

[30] Foreign Application Priority Data

Aug. 5, 1985 [JP] Japan ................................. 60-172660

[51] Int. Cl.⁴ .................. C07D 501/20; A61K 31/545
[52] U.S. Cl. ..................................... 514/202; 540/222
[58] Field of Search ......................... 540/222; 514/202

[56] References Cited

U.S. PATENT DOCUMENTS

| 4,368,198 | 1/1983 | Yamada et al. | 514/202 |
| 4,500,716 | 2/1985 | Kinast | 540/222 |
| 4,515,788 | 5/1985 | Takaya et al. | 540/222 |
| 4,634,697 | 1/1987 | Hamashima | 540/222 |

Primary Examiner—Donald G. Daus
Assistant Examiner—Barbara Cassatt
Attorney, Agent, or Firm—Wenderoth, Lind & Ponack

[57] ABSTRACT

An antibacterial 3-(alkylcarbamoyloxymethyl)-3-cephem-4-carboxylic acid or its derivatives represented by the following formula

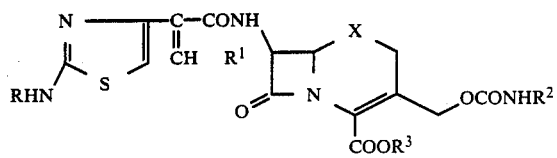

(wherein
R is hydrogen or an amino-protecting group,
$R^1$ and $R^2$ each is the same or different 1C to 8C alkyl,
$R^3$ is hydrogen, a salt or ester forming atom or group, and
X is sulfur or sulfinyl), a pharmaceutical composition containing the same, a method for treating a bacterial infection with the same, and a method for preparing the same are disclosed.

5 Claims, No Drawings

ALKYLCARBAMOYLOXYMETHYLCEPHEM COMPOUNDS

This invention relates to an alkylcarbamoyloxymethylcephem compound. More specifically, it relates to 7β-[2-(2-aminothiazol-4-yl)-2-alkenamido]-3-(alkylcarbamoyloxymethyl)-3-cephem-4-carboxylic acid or its derivative represented by the following formula

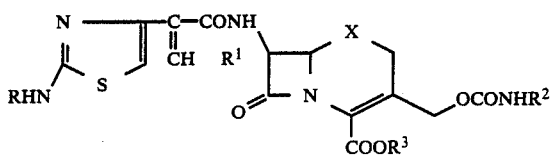

(wherein
R is hydrogen or an amino-protecting group,
$R^1$ is 1C to 8C alkyl,
$R^2$ is 1C to 8C alkyl,
$R^3$ is hydrogen, a salt- or ester-forming atom or group, and
X is sulfur or sulfinyl)

[EXPLANATION OF THE SYMBOLS]

In above formula (I), the amino-protecting group R may contain 1 to 19 carbon atoms and can be 1C to 8C alkyl (e.g., trichloroethyl, methoxyethoxymethyl, tetrahydropyranyl), 7C to 19C aralkyl (e.g., diphenylmethyl, trityl, methoxybenzyl), 1C to 8C alkylthio, 6C to 8C arylthio (e.g., nitrophenylthio), 5C to 8C cycloalkylidene, 1C to 8C acyl [e.g., 1C to 8C alkanoyl (e.g., formyl, acetyl, chloroacetyl, trifluoroacetyl), 2C to 8C alkoxycarbonyl (e.g., that having methyl, ethyl, propyl, cyclopropylethyl, isoproyl, butyl, isobutyl, pentyl, hexyl, trichloroethyl, pyridylmethyl, cyclopentyl, or cyclohexyl as the lower alkyl part), 8C to 19C aralkoxycarbonyl (e.g., that having benzyl, diphenylmethyl, or nitrobenzyl as the aralkyl part), 7C to 12C aroyl (e.g., benzoyl, nitrobenzoyl), succinyl, phthaloyl], 3 C to 9 C trialkylsilyl, 3 C to 9C alkoxydialkylsilyl, 3C to 9C trialkylstannyl, or the like, and that forming RNH being 1C to 8C alkylideneamino or 7C to 12C aralkylideneamino (e.g., benzylideneamino, methylbenzylideneamino, nitrobenzylideneamino).

The alkyl as $R^1$ or $R^2$ is an unsubstituted 1C to 8C alkyl (e.g., methyl, ethyl, propyl, isopropyl, butyl, isobutyl, tertbutyl, pentyl, hexyl, isooctyl).

The ester-forming group $R^3$ can be one useful for carboxy protection in the penicillin and cephalosporin fields known which can be introduced and removed without adverse effect on other parts of the molecule. It is preferable that having 2C to 19C and forming, for example, a 1C to 8C alkyl ester (e.g., methyl, methoxymethyl, ethyl, ethoxymethyl, trichloroethyl, iodoethyl, propyl, isoproyl, ethoxyethyl, methylthioethyl, methanesulfonylethyl, butyl, isobutyl, tert-butyl, or hexyl ester), 2C to 8C alkenyl ester (e.g., vinyl, propenyl, or allyl ester), 7C to 19C aralkyl ester (e.g., benzyl, methylbenzyl, dimethylbenzyl, methoxybenzyl, ethoxybenzyl, nitrobenzyl, aminobenzyl, diphenylmethyl, phenethyl, trityl, di-tert-butylhydroxybenzyl, phthalidyl, or phenacyl ester), 6C to 12C aryl ester (e.g., phenyl, tolyl, diisopropylphenyl, xylyl, trichlorophenyl, pentachlorophenyl, or indanyl ester), ester with a 1C to 12C N-hydroxyamino compound (e.g., ester with acetone oxime, acetophenone oxime, acetaldoxime, N-hydroxysuccinimide, or N-hydroxyphthalimide), 3C to 12C silyl ester (e.g., trimethylsilyl, tert-butyldimethylsilyl, or dimethylmethoxysilyl ester), 3C to 12C stannyl ester (e.g., trimethylstannyl ester), or the like. The carboxy protecting ester group may have a substituent. This group is absent in the objective compounds. So, its structure has not in itself any specific meaning as long as it protects the carboxy during the synthesis. Thus it can be replaced by a wide variety of equivalent groups (e.g., amide or acid anhydride with carbonic or carboxylic acid) or the like.

The salt forming group $R^3$ can preferably be that forming a pharmaceutically acceptable ion and belonging to group I to III and period 2 to 4 in the Periodical Table. This can preferably be a light metal [e.g., alkali metal (e.g., sodium, potassium, lithium), alkaline earth metal (e.g., magnesium, calcium), aluminum, or the like]. A salt with 1 C to 12C alkylamine (e.g., trimethylamine, triethylamine, methylmorpholine) or 4C to 9C aromatic base (e.g., pyridine, collidine, picoline, quinoline, dimethylaniline) is available for synthetic purposes.

The ester forming group $R^3$ can be a so-called pharmaceutically acceptable ester group, for example, a 1-oxygenated-2C to 15C alkyl {e.g., alkanoyloxyalkyl (e.g., acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl), 3C to 15C alkoxycarbonyloxyalkyl (e.g., ethoxycarbonyloxyethyl, isopropoxycarbonyloxyethyl, isopropoxycarbonyloxypropyl, tert-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl), 2C to 8C alkoxyalkyl (e.g., methoxymethyl), 4C to 8C 2-oxacycloalkyl (e.g., tetrahydrofuranyl, tetrahydropyranyl)}, 8C to 12C aralkyl (e.g., phenacyl, phthalid-yl), 6C to 12C aryl (e.g., phenyl, xylyl, indanyl), 2C to 12C alkenyl (e.g., allyl, 5-methyl-2-oxo-1,3-dioxol-4-ylmethyl), or the like.

In above definition of the symbols, the carbon number referred to includes that for the substituent.

The alkyl part can be a straight, branched, or cyclic alkyl which may be substituted (e.g., by hydroxy, alkoxy, acyloxy, amino, acylamino, dialkylamino, cyano, carboxamino, formimidoylamino, oxo, acyl, alkyl, halogen, protected carboxy, carbamoyl).

The acyl part can also be straight, branched, or cyclic alkanoyl, monocyclic or dicyclic aroyl, aralkanoyl, arylalkenoyl, alkylsulfonyl, arylsulfonyl, carbamoyl, carbalkoxy, carbaralkoxy, sulfo, or the like acyl, which may optionally have nitrogen, oxygen, or sulfur as a hetero atom in its skeleton. The acyl may have a substituent as defined above.

The aryl part can be 5 to 6 membered monocyclic or bicyclic and carbocyclic or heterocyclic aryl and may have a substituent as given above. The typical heterocyclic group are furyl, thienyl, pyrrolyl, oxazolyl, thiazolyl, imidazolyl, oxadiazolyl, thiadiazolyl, triazolyl, thiatriazolyl, tetrazolyl, pyridyl, quinolyl, pyridopyridyl, and the like.

[SPECIFIC COMPOUNDS]

A preferable compound (I) has hydrogen or tert-butoxycarbonyl as R, methyl, ethyl, propyl, or isopropyl as $R^1$, methyl, ethyl, propyl, or isopropyl as $R^2$, hydrogen, sodium, diphenylmethyl, a pharmacologically acceptable ester group (e.g., acetoxymethyl, 1-

(acetoxy)ethyl, 1-(cyclohexylcarbonyloxy)-1-cyclohexylmethyl, 1-(cyclohexylmethoxycarbonyloxy)propyl, 1-(cyclohexyloxycarbonyloxy)ethyl, 1-(ethoxycarbonyloxy)ethyl, 1-(isopentyloxycarbonyloxy)propyl, 1-(isopropoxycarbonyloxy)ethyl, 1-(isopropyloxycarbonyloxy)propyl, (4-methyl-2-oxo-1,3-dioxol-5-yl)methyl, pivaloyloxymethyl, 1-(pivaloyloxy)ethyl, or 1-(tert-butoxycarbonyloxy)ethyl as $R^3$, and sulfur as X.

A representative compound has R as hydrogen, $R^1$ as methyl, $R^2$ as methyl, and $R^3$ as hydrogen, sodium, acetoxymethyl, 1-(acetoxy)-ethyl, 1-(cyclohexylcarbonyloxy)-1-cyclohexylmethyl, 1-(cyclohexyloxycarbonyloxy)ethyl, 1-(ethoxycarbonyloxy)ethyl, 1-(isopropoxycarbonyloxy)ethyl, or pivaloyloxymethyl; R as hydrogen, $R^1$ as ethyl, $R^2$ as methyl, and $R^3$ as hydrogen, sodium, acetoxymethyl, 1-(acetoxy)ethyl, 1-(ethoxy-carbonyloxy)ethyl, 1-(isopentyloxycarbonyloxy)propyl, 1-(isopropoxycarbonyloxy)propyl, (4-methyl-2-oxo-1,3-dioxol-5-yl)methyl, 1-(pivaloyloxy)ethyl, pivaloyloxymethyl, or 1-(tert-butoxycarbonyloxy)ethyl; R as hydrogen, $R^1$ as ethyl, $R^2$ as ethyl, and $R^3$ as hydrogen, sodium, or pivaloyloxymethyl; R as hydrogen, $R^1$ as ethyl, $R^2$ as isopropyl, and $R^3$ is hydrogen, sodium, pivaloyloxymethyl, or 1-(cyclohexylmethoxycarbonyloxy)propyl; R as hydrogen, $R^1$ as propyl, $R^2$ as methyl, and $R^3$ as hydrogen, sodium, or pivaloyloxymethyl; or R as hydrogen, $R^1$ as isopropyl, $R^2$ as methyl, and $R^3$ as hydrogen, sodium, or pivaloyloxymethyl.

[PRIOR ARTS]

Some 3-alkylcarbamoyloxymethylcephalosporins are described in U.S. Pat. No. 3,484,437. Some compounds closely related to the free carboxylic acid of Compound (I) are described in U.S. Pat. Nos. 4,014,869 and 4,416,880. However, compound (I) having alkyl as $R^2$ and especially a pharmaceutically acceptable ester group as $R^3$ has never been disclosed.

[TECHNICAL MERITS]

The compounds (I) having methyl as $R^2$ is superior to those having hydrogen as $R^2$ of copending U.S. application Ser. No. 845,305, filed Mar. 27, 1986 in their oral availability (represented by blood level maximum of 28.7 μg/ml for a compound having methyl as $R^2$ whereas that of 9.3 μg/ml for a compound having hydrogen as $R^2$ when $R^1$ is ethyl and $R^3$ is pivaloyloxymethyl), antibacterial potency against Gram-positive bacteria, excretion, distribution, or the like characteristics.

[USE]

A free carboxy-, salt-, or pharmacological ester-compound (I) is a potent antibacterial against aerobic or anaerobic bacteria. It may be used as a bacteriocidal, bacteriostatic, disinfecting, or antiperishing agent, bacterial growth inhibitor in human, animal, plant, or perishable subjects, a human or animal growth promoting additive in foodstuffs, or an agent for treating or preventing a human, veterinary, or poultry infection caused by sensitive bacteria and for testing senstitivity of bacteria to the antibacterial (I).

Thus, the said compound (I) is an antibacterial against aerobic Gram-positive bacteria (e.g., *Bacillus cereus, Bacillus subtilis, Corynebacterium diphtheriae, Staphylococcus aureus, Staphylococcus epidermidis, Streptococcus pneumoniae, Streptococcus pyogenes, Streptococcus viridans, Streptococcus faecalis*) and Gram-negative bacteria (e.g., *Citrobacter diversus, Citrobacter freundii, Enterobacter aerogens, Enterobacter cloacae, Escherichia coli, Haemophilus influenzae, Klebsiella pneumoniae, Neisseria gonorrhoeae, Neisseria meningitidis, Proteus mirabilis, Morganella morganii, Proteus vulgaris, proteus rettgeri, Providencia stuartii, Pseudomonas aeruginosa, Salmonella paratyphi, Salmonella typhi, Serratia marcescens, Shigella sonnei, Yersinia enterocolitica*), and anaerobic bacteria (e.g., *Clostridium difficile, Clostridium novyi, Eubacterium cylindroides, Bacteroides fragilis, Fusobacterium nucleatum, Propionibacterium* spp., Veillonella parvula).

[METHOD FOR TREATMENT]

Compound (I) as carboxylic acid or its light metal salt can be given intravenously, intramuscularly or subcutaneously (as e.g., solution, suspension), or orally, if required in admixture with an excipient (e.g., solubilizing agent, emulsifying agent). A pharmacological ester (I) can be given intravenously, intramuscularly, subcutaneously, orally (as e.g., capsule, dry syrup, emulsion, powder, solution, suspension, tablet, troche), externally, or topically (as e.g., ear, nasal, or ocular drug, ointment, injection, pap preparation, spray, suppository).

A protected compound (I) is also useful as a starting material for synthesizing other antibacterials or as an agent for testing sensitivity of bacteria.

This invention also provides a method for treating or preventing a human or veterinary bacterial infection (e.g., abscess, bronchitis, dermatitis, ear infections, empyema, enteritis, gastroenteritis, nasopharyngitis, osteomyelitis, pneumonitis, pneumonia, pustulosis, pyelonephritis, respiratory tract infection, rhinitis, septicemia, tonsillitis, ulceration, urinary tract infection, wound and soft tissue infection) caused by sensitive bacteria by administering an effective amount of the said compound (I) at a typical daily dose of 0.1 to 6 gram (injection), 0.1 to 4 gram (orally), or 0.1 to 10 mg (topically), if required formulating with a conventional additive, coacting substance (e.g., other antibacterial), or the like.

This invention also provides an antibacterial pharmaceutical composition containing the said compound (I) in a various enteral or parenteral dosage form, solely or in admixture with a carrier or coacting substance. The composition may contain 0.01 to 99% of compound (I) dissolved, dispersed, or suspended in a solid or liquid pharmaceutical carrier.

The composition may be a solid preparation (e.g., capsule, dry syrup, granule, lyophilized material, pellet, pill, powder, suppository, troche, tablet) or liquid preparation (e.g., dispersion, elixir, emulsion, inhalant, injection, ointment, suspension, syrup, solution). The capsule, granule, and tablet may be coated. They can be in a unit dosage form.

The carrier is inert to both the compound (I) and patients. Representative examples of such carrier include, among others, for a solid preparation, a binder (e.g., acacia, carboxymethylcellulose, gelatin, glucose, polyvinylpyrrolidone, sodium alginate, sorbitol, starch, syrup, tragacanth), bulking agent (e.g., bentonite, calcium carbonate, calcium phosphate, glycine, kaolin, lactose, polycarboxymethylene, salt, sorbitol, starch, sugar, talc), diluent (e.g., calcium carbonate, kaolin, lactose, starch, sucrose), disintegrator (e.g., agar, carbonate, sodium laurylsulfate, starch), lubricant (e.g., boric acid, cacao oil, magnesium stearate, paraffin, polyethyleneglycol, silica, sodium benzoate, stearic acid, talc), and wetting agent (e.g., hydroxypropylcellulose); for a solution, a solvent (e.g., alcohol, buffer, methyl oleate, peanut oil, sesame oil, water), emulsifying agent (e.g., acacia, lethicin, sorbitan monooleate), suspending agent (e.g., aluminum stearate gel, carboxymethylcellulose, gelatin, glucose, hydrogenated fats, hydroxyethylcellulose, methyl cellulose, sorbitol, sugar syrup), buffer, dispersing agent, and solubilizing agent: and for both, a perservative (e.g., methyl or ethyl p-hydroxybenzoate, sorbic acid), absorption promoter (e.g., glycerin mono- or di-octanoate), antioxidant, aromatic substance, analgesic, edible coloring agent, stabilizing agent, or the like.

The said pharmaceutical preparation can be prepared in a conventional manner.

[SYNTHESIS]

The compound (I) according to this invention can be prepared by a conventional method as given below.

(1) Amidation

A conventional amidation of amine (II) (i.e., $7\beta$-amino-3-alkylcarbamoyloxymethyl-3-cephem-4-carboxylic acid) or its reactive derivative with carboxylic acid (III) (i.e., optionally protected 2-(2-aminothiazol-4-yl)-2-alkenoic acid) or its reactive derivative gives compound (I) or its derivative.

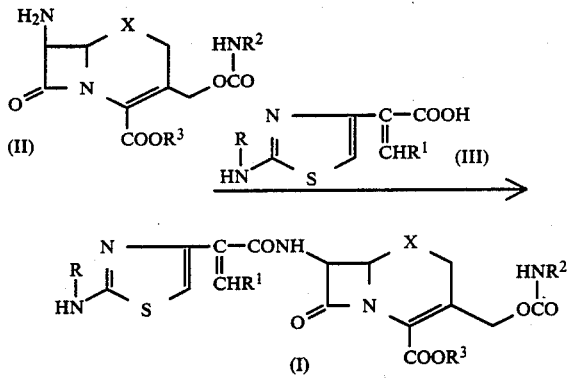

A typical reactive derivative of amine (II) has 7-amino activated by silyl (e.g., trimethylsilyl, methoxydimethylsilyl, tert-butyldimethylsilyl), stannyl (e.g., trimethylstannyl), alkylene (as a part of enamino consisting of the amino with, e.g., aldehyde, acetone, acetylacetone, acetoacetate ester, acetoacetonitrile, acetoacetanilide, cyclopentanedione, acetylbutyrolactone), alkyliene (e.g., 1-haloalkylidene, 1-haloaralkylidene, 1-alkoxyalkylidene, 1-alkoxyaralkylidene, 1-alkoxy-1-phenoxyalkylidene, alkylidene, aralkylidene), acid (as a salt of the amino with, e.g., mineral acid, carboxylic acid, sulfonic acid), easily removable acyl (e.g., alkanoyl), or the like and that protected at other function of the molecule.

The carboxylic acid (III) is used in the presence of a known condensing reagent [for example, carbodiimide (e.g., N,N'-diethylcarbodiimide, N,N'-dicyclohexylcarbodiimide), carbonyl compound (e.g., carbonyldiimidazole), isoxazolinium salt, acylamino compound (e.g., 2-ethoxy-1-ethoxycarbonyl-1,2-dihydroquinoline), halide (e.g., cyanuric chloride, diphenylphosphoryl chloride, methanesulfonyl chloride, oxalyl chloride, phosphorus oxychloride, thionyl chloride, tripyridiniumtriazine trihalide), or the like]. This reaction may preferably be carried out in an aprotic solvent using carboxylic acid (III) (1 to 2 molar equivalents) and a condensing reagent (1 to 2 molar equivalents) per amine (II).

The reactive derivative includes acid anhydride {for example, symmetric anhydride, mixed anhydride [with a mineral acid (e.g., phosphoric acid, sulfuric acid, carbonic half ester), organic acid (e.g., lower alkanoic acid, aralkanoic acid, lower alkyl- or aryl-sulfonic acid)], intramolecular acid anhydride (e.g., ketene, isocyanate), acid halide (i.e., mixed anhydride of the acid with hydrogen halide)}, reactive ester [enol ester (e.g., vinyl ester, isopropenyl ester), aryl ester (e.g., phenyl ester, halophenyl ester, nitrophenyl ester), heterocyclic ester (e.g., pyridyl ester, 1-hydroxybenzotriazolyl ester), ester with N-hydroxy compound, ester with diacylhydroxylamine (e.g., N-hydroxysuccinimidoyl ester, N-hydroxyphthalimidoyl ester), thiol ester (e.g., aralkylthiol ester, heterocyclic thiol ester), or the like], reactive amide [e.g., aromatic amide (e.g., amide with imidazole, triazole, 2-ethoxy-1-ethyl-1,2-dihydroquinoline), diacylanilide], and the like. The acid scavenger to be used with the said reactive derivatives include an inorganic base (e.g., oxide, hydroxide, carbonate, hydrogen carbonate, or the like of alkali metal, alkaline earth metal), organic base (e.g., tert-amine, aromatic base), oxirane (e.g., alkylene oxide, aralkylene oxide), adsorbent (e.g., Celite), or the like. This reaction may preferably be carried out in an aprotic solvent using a reactive derivative of carboxylic acid (II) (1 to 2 molar equivalents) and an acid scavenger (0 to 2 molar equivalents) per amine (II). Acid halide and enzymatically reactive ester can be used in an aqueous solvent.

(2) Alkylcarbamic ester formation

A 3-hydroxymethyl compound (II) (i.e., $7\beta$-[2-(2-aminothiazol-4-yl)-2-alkenamido]-3-hydroxymethyl-3-cephem-4-carboxylic acid) or its derivative is conventionally esterified with an alkylcarbamoylating reagent of the formula $R^2$NHCO-Hal or $R^2$NCO (wherein $R^2$ is as defined in claim 1 and Hal is halogen) to afford compound (I).

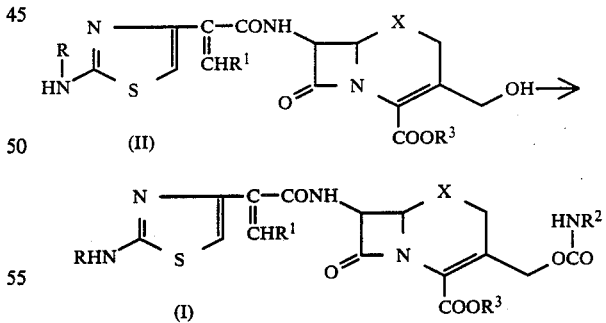

Here, the alkylcarbamoylating reagent can be a conventional alkylcarbamoylating reagent (e.g., alkyl isocyanate, alkylcarbamoyl halide). The reagent can be used conventionally, for example, in the presence of a subreagent [e.g., acid scavenger (e.g., aromatic base, tertiary amine), Lewis acid (e.g., aluminum chloride, bis(alkylstannyl)oxide), or the like]. This reaction is usually carried out in a solvent at 0° C. to 50° C. for 30 minutes to 10 hours to give the objective alkylcarbamic ester.

(3) Esterification

A compound (I) having hydrogen as $R^3$ can be esterified conventionally in an inert solvent to give an ester compound (I), for example, by a method as given below:

(a) A reaction of the halide, sulfonate, or the like of the ester group with an alkali metal salt of the carboxylic acid at $-50°$ C. to $50°$ C.;

(b) A reaction of the alcohol of the ester group with the carboxylic acid or its reactive derivative in the presence of a condensing reagent; or (c) A reaction of a diazo compound of the ester group with the carboxylic acid at $0°$ C. to $50°$ C.

Especially important esterification is that comprises treating 7β-[2-(2-amino-thiazol-4-yl)-2-alkenamido]-3-alkylcarbamoyloxymethyl-3-cephem-4-carboxylic acid represented by the following formula:

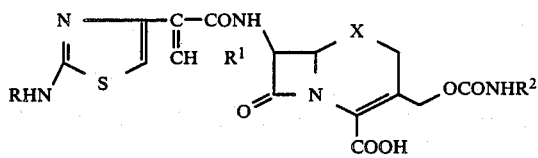

or its salt with a halide of a pharmaceutically acceptable group represented by the formula $R^3$—Hal (wherein $R^3$ is a pharmaceutically acceptable ester group and Hal is halogen) in the presence of an acid scavenger to afford the corresponding pharmaceutically acceptable ester (I).

(4) Amino- and/or Carboxy Deprotection

A compound (I) is usually produced through its amino- and/or carboxy-protected compound. So, on some stage to the objective compound, a deprotection is a requisite step in its production. One of the preferable processes is a deprotection of an amino- and/or carboxy-protected compound using acid, aqueous base, or Lewis acid in an inert solvent, as given below:

(4-a) Deprotection of Protected Carboxy

A compound (I) having protected carboxy can be deprotected conventionally in an inert solvent to give carboxylic acid (I). This deprotection includes, for example, the following procedures:

(a) A highly reactive ester, anhydride, etc., as a carboxy-protecting group can be deprotected by contacting it with acid, base, buffer solution, ion-exchange resin, or the like in an aqueous solvent. Some insufficiently reactive groups may be activated conventionally to deprotect easily (e.g., trichloroethyl ester with metal and acid; p-nitrobenzyl ester by hydrogenation, dithionate, or metal and acid; and phenacyl ester by irradiation);

(b) An aralkyl ester as a carboxy-protecting group can be deprotected by a conventional hydrogenation in the presence of a catalyst (e.g., palladium, platinum, nickel);

(c) A tert-alkyl ester, 2-alkenyl ester, aralkyl ester, sulfonylethyl ester, tert-alkoxycarbonylamido, aralkoxycarbonylamido, or the like as an amino- or carboxy-protecting group may be deprotected by treating, for example, with a mineral acid, Lewis acid, (e.g., aluminum chloride, tin tetrachloride, titanium tetrachloride), sulfonic acid (e.g., benzenesulfonic acid, methanesulfonic acid, trifluoromethanesulfonic acid), strong carboxylic acid (e.g., trifluoroacetic acid), or the like, if required in the presence of a cation scavenger (e.g., anisole, benzenethiol);

(d) A 2-alkenyl ester as a carboxy-protecting group can be deprotected by the action of triarylphosphine-palladium complex;

(e) A phenacyl ester, 2-alkenyl ester, hydroxyaralkyl ester, or the like as a carboxy-protecting group can be deprotected by the action of a base or nucleophilic reagent; or (f) Other equivalent deprotection of a carboxy-protecting group.

(4-b) Deprotection of an Amino-Protecting Group

A compound (I) having an amino-protecting group can be deprotected conventionally in an inert solvent, for example, as given below:

(a) An alkoxycarbonyl group (e.g., tert-butoxycarbonyl) as an amino-protecting group can be deprotected with a strong acid (e.g., trifluoroacetic acid, trifluoromethanesulfonic acid), Lewis acid (e.g., aluminum chloride, tin tetrachloride, titanium tetrachloride, zinc chloride), or the like acid at $-30°$ C. to $50°$ C., if required in the presence of a cation scavanger (e.g., anisole, benzenethiol); (b) An aralkoxycarbonyl (e.g., carbobenzoxy, methylcarbobenzoxy, diphenylmethoxycarbonyl) as an amino-protecting group can be removed by the action of hydrogen (e.g., catalytic hydrogenation using palladium, nickel, or the like catalyst) or the said Lewis acid and cation scavenger at $0°$ C. to $50°$ C.; (c) A lower alkanoyl (e.g., formyl, acetyl, chloroacetyl), Schiff base forming group (i.e., a divalent carbon function, e.g., ethylidene, propylidene, benzylidene, substituted benzylidene), aralkyl (e.g., trityl, substituted trityl), arylthio (e.g., phenylsulfenyl), tetrahydropyranyl, silyl or stannyl (e.g., trimethylsilyl, trimethylstannyl), or the like group as an amino-protecting group can be deprotected by the action of acid (e.g., hydrochloric acid, sulfuric acid, methanesulfonic acid) at $-20°$ C. to $50°$ C.; or (d) Other specific method for some specific group (e.g., thiourea or N-alkylcarbamate for haloacetyl, hydrazine for dibasic acyl, phosphorus pentachloride and alkanol for amide).

(5) Salt Formation

A compound (I) having hydrogen as $R^3$ can form a salt compound (I) (wherein $R^3$ is a salt forming group) with a base or with a salt of weakly acidic carboxylic acid by an ion exchange reaction. The procedure can be that conventional in the art, e.g., by neutralizing the free acid with a base (e.g., light metal hydroxide, carbonate, or hydrogen carbonate) or by treating with light metal lower carboxylate (e.g., sodium acetate, sodium lactate, sodium 2-ethylhexanoate) in a polar organic solvent (e.g., alcohol, ketone, ester) and then adding a sparingly dissolving solvent to separate the salt. The reaction time is usually 1 to 10 minutes at lower than $50°$ C., but it may be longer if no appreciable side reaction occurs.

(6) Protection of Amino

The amino group in compound (I) can be protected at its amino in a conventional manner as given below:

(a) An alkoxycarbonyl, aralkoxycarbonyl, alkanoyl, trialkylsilyl, or the like group as an amino-protecting group can be introduced by treating the amine with a halide or symmetric or asymmetric anhydride of the protecting group (1 to 5 equivalents) in the presence of an acid scavenger at −30° C. to 50° C.; (b) An alkoxycarbonyl, aralkoxycarbonyl, alkanoyl, arylsulfenyl, aralkyl, trialkylsilyl, trialkylstannyl, or the like group as an amino-protecting group can be introduced by treating the amine with a halide of the group (1 to 5 molar equivalents) in the presence of an acid scavenger (1 to 10 molar equivalents) in a solvent at −30° C. to 100° C.; (c) A tetrahydropyranyl, tetrahydrofurayl, or the like group as an amino-protecting group can be introduced by reacting the amine with dihydropyran, dihydrofuran, etc., in a solvent; or (d) A trialkylsilyl group as an amino-protecting group can be introduced by treating the amine with disilazane, acetamide, or the like compound (e.g., hexamethyldisilazane, bistrimethylsilylacetamide).

(7) Oxidation to Sulfoxide

A compound (I) having a sulfide group in its molecule can be oxidized conventionally, for example, with the following oxidizing reagent to give the corresponding sulfoxide (I) (when the starting sulfide has a double bond at position 2, this migrates to position 3 in the sulfoxide product). (a) Peracid (e.g., industrially available permineral acid, percarboxylic acid, persulfonic acid); (b) Ozone; (c) Hydrogen peroxide; or (d) Peroxide (e.g., boron peroxide, nickel peroxide, sodium peroxide, urea peroxide).

Thus, compound (I) having sulfur as X is treated with an oxidizing reagent (e.g., hydrogen peroxide, percarboxylic acid, inorganic percid) in an inert solvent (e.g., halogenohydrocarbon, ester, water) to give the corresponding sulfoxide (I). Preferably the starting compound (I) is oxidized with the oxidizing reagent (1 to 2 molar equivalents) at −10° C. to 50° C. to give the sulfoxide. The reaction can be carried out, if required, in the presence of a catalyst (e.g., alkanoic acid, phosphoric acid, phosphoric ester, a salt of acid of the VIIth group atom in the periodical table).

(8) Reduction of Sulfoxide

Compound (I) having sulfinyl in the molecule can be reduced conventionally to give the corresponding sulfide (I).

Thus, compound (I) having sulfinyl as X is treated with 2 to 5 molar equivalents of a reducing reagent (e.g., trivalent phosphorus compound, stannous compound, hydrogen iodide) in an inert solvent (e.g., dimethylformamide, dichloromethane, dioxane) at −20° to 50° C. to give the corresponding sulfide (I).

(9) Reaction Conditions

The said syntheses (1) to (8) are usually carried out at −70° C. to 100° C., especially −30° C. to 50° C., for 10 minutes to 30 hours. Preferably, these are carried out under dry condition in a solvent. Other conventional conditions are applicable.

The reaction solvent can be a hydrocarbon (e.g., pentane, hexane, octane, benzene, toluene, xylene), halogenohydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), amide (e.g., formamide, acetamide, dimethylformamide, dimethylacetamide, hexamethylphosphorotriamide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water, or the like industrial solvent or a mixture.

(10) Work Up

The objective products can be recovered from the reaction mixture after removing contaminants (e.g., unreacted starting material, by-products, solvents) by a conventional method (e.g., extracting, evaporating, washing, concentrating, precipitating, filtrating, drying) and isolated by a usual work up (e.g., adsorbing, eluting, distilling, precipitating, separating, chromatographying).

Among the geometric isomers in relation to the trisubstituted double bond in the side chain at position 7, that having thiazole ring and hydrogen in the cis position is more useful than that having them in the trans position in antibacterial potency.

(11) EXAMPLES

Following examples illustrate the embodiment of the invention. The physical constants of the products are listed in the tables. In the tables, IR shows wave numbers in $cm^{-1}$ scale and NMR shows δ values (chemical shift) in ppm scale and J values (coupling constant) in Hz scale.

In the examples, the amount shown by part is the weight of the substance per 1 weight of the betalactam starting material. The equivalent is the molar number of the substance per 1 mole of the starting betalactam.

The work up procedure in the examples is usually carried out conventionally as follows: The reaction mixture is diluted with water, acid, dichloromethane, or the like. When the product is neutral, the organic layer is taken, washed with water, dried, and concentrated under reduced pressure to give residual mass. The mass is, if required after purifying by silica gel chromatography, crystallized, precipitated or filtrated to afford the product. The physical contants of the products are listed on the tables after Examples. All are the cis isomer in relation to the double bond in the side chain at position 7 unless otherwise specified.

| [Abbreviations] | |
|---|---|
| AOE = 1-(acetoxy)ethyl | AOM = acetoxymethyl |
| BCE = 1-(tert-butoxycarbonyloxy)ethyl | |
| BH = diphenylmethyl | BOC = tert-butoxycarbonyl |
| Bu = butyl | |
| DOL = (4-methyl-2-oxo-1,3-dioxol-5-yl)methyl | |
| ECE = 1-(ethoxycarbonyloxy)ethyl | |
| Et = ethyl | |
| HCE = 1-(cyclohexyloxycarbonyloxy)ethyl | |
| HOH = 1-(cyclohexylcarbonyloxy)-1-cyclohexylmethyl | |
| HmCP = 1-(cyclohexylmethoxycarbonyloxy)propyl | |
| ICE = 1-(isopropoxycarbonyloxy)ethyl | |
| ICP = 1-(isopropoxycarbonyloxy)propyl | |
| Me = methyl | |
| POE = 1-(pivaloyloxy)ethyl | |
| POM = pivaloyloxymethyl | |
| PeCP = 1-(isopentyloxycarbonyloxy)propyl | |
| Ph = phenyl | Pr = propyl |
| SO = 1-oxide | |
| Chf = chloroform | DCM = dichloromethane |
| THF = tetrahydrofuran | DMA = N—dimethyl-acetamide |
| DMF = N,N—dimethylformamide | |
| S.M. = starting material | Exp. No. = Example No. |
| TFA = trifluoroacetic acid | m-CPBA = m-chloroperbenzoic acid |
| Yld. = yield | |
| nd = not determned | Temp = temperature |
| | hr = hour |

| [Abbreviations] | |
|---|---|
| rt | = room temperature |

EXAMPLE 1

(Amidation)

A 7β-amino compound (2) (1 equivalent) is treated with a carboxylic acid (3) corresponding to the 7β-side chain or its reactive derivative to give amide (1), for example, by a conventional method as exemplified below:

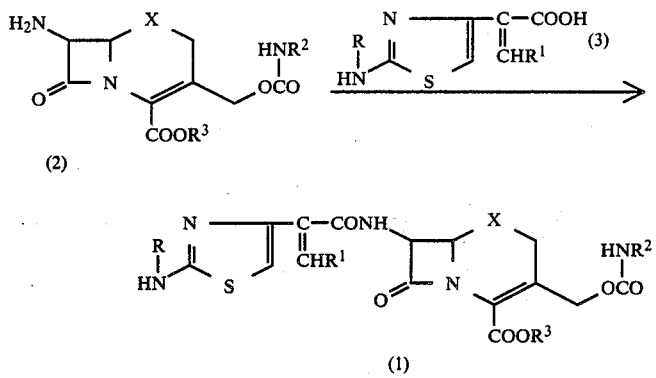

(1) In a mixture of carbon tetrachloride (30 parts), N-methylmorpholine (1.5 equivalents), trisdiethylaminophosphine (1.1 equivalents), and carboxylic acid (3) (1.1 equivalents), kept at −20° C. to 10° C. for 1 to 5 hours.

(2) In a mixture of dichloromethane (5 to 30 parts), trifluoroacetic acid anhydride (1.5 equivalents), pyridine (3 equivalents), and carboxylic acid (3) (1.5 equivalents), stirred at 0° C. to room temperature for 1 to 5 hours.

(3) In a mixture of dichloromethane (10 to 30 parts), diphenylphosphoryl chloride (1.2 equivalents), N-methylmorpholine (2.5 equivalents), and carboxylic acid (3) (1.2 equivalents), stirred at −50° to 0° C. for 1 to 3 hours.

(4) In a mixture of dichloromethane (10 to 50 parts), cyanuric chloride (1.1 equivalents), pyridine (4 equivalents), and carboxylic acid (3) (1.1 equivalents), stirred at −30° C. to 10° C. for 5 minutes to 2 hours.

(5) In a mixture of dichloromethane (3 to 30 parts), phosphorus oxy-chloride (1.1 equivalents), triethylamine (1.5 equivalents), and carboxylic acid (3) (1.1 equivalents), stirred at −10° C. to 10° C. for 20 minutes to 2 hours.

(6) Amine (2) is treated with trimethylsilyl chloride and an acid scavenger to obtain the corresponding N-trimethylsilylamino compound and this is treated with phosphorus oxychloride (1.5 equivalents), carboxylic acid (3) (1.2 equivalents), and dimethylaniline (4equivalents) in dichloromethane (5 to 30 parts) at 0° C. to room temperature for 30 minutes to 2 hours.

(7) In a mixture of dichloromethane (5 to 30 parts), thionyl chloride (1.5 equivalents), pyridine (2.5 equivalents), and carboxylic acid (3) (1.1 equivalents), stirred at −30° C. to 0° C. for 1 to 5 hours.

(8) In a mixture of chloroform (3 to 30 parts), toluene (1 part), carboxylic acid (3) (1.1 equivalents), picoline (2 equivalents), and oxalyl chloride (1 equivalents), stirred at −50° C. to 10° C. for 10 minutes to 2 hours.

(9) In a mixture of dichloromethane (20 to 50 parts), 1-ethoxycarbonyl-2-ethoxy-1,2-dihydroquinoline (2.1 equivalents), N,N'-dicyclo-hexylcarbodiimide (2.5 equivalents), and carboxylic acid (3) (2 equivalents), stirred at room temperature for 1 to 15 hours.

(10) In a mixture of dichloromethane (3 to 20 parts), carboxylic acid (3) (1.1 equivalents), 1,3,5-tripyridiniumtriazine trichloride (4 equivalents), stirred at −10° C. to 10° C. for 1 to 5 hours.

(11) In a mixture of carbonyldiimidazole (1.1 equivalents), tetrahydrofuran (5 to 50 parts), dimethylacetamide (5 parts), and carboxylic acid (3) (1.1 equivalents), stirred at 0° C. to room temperature for 1 to 5 hours.

(12) In a mixture of dimethylformamide (5 to 30 parts), dimethylaniline (1.3 equivalents), carboxylic acid (3), and the Vilsmeyer reagent made from dimethylformamide (1.1 equivalents), stirred at room temperature for 1 to 5 hours.

(13) In a mixture of dichloromethane (10 to 50 parts), dimethylformamide (5 parts), N,N'-dicyclohexylcarbodiimide (1.1 equivalents), picoline (1.2 equivalents), and carboxylic acid (3) (1.1 equivalents), heated under reflux for 2 to 24 hours.

(14) To a solution of 2-(2-tert-butoxycarbonylaminothiazol-4-yl)-2-pentenoic acid (1.49 g) in dichloromethane (60 ml) are added triethylamine (0.83 ml) and methanesulfonyl chloride (0.4 ml) at −65° C., and the mixture is stirred for 3 hours at −65° C. To the mixture is added diphenylmethyl 7β-amino-3-methylcarbamoyloxymethyl-3-cephem-4-carboxylate (2.26 g) and N-methylmorpholine (0.55 ml) in dichloromethane (60 ml). After 2 hours, the reaction mixture is neutralized with 10% citric acid, washed with water, dried, and concentrated to give diphenylmethyl 7β-[2-(2-tert-butoxycarbonylaminothiazol-4-yl)-2-pentenoylamino]-3-methylcarbamoyloxymethyl-3-cephem-4-carboxylate (3.12 g). Yield: 85%.

(15) To a mixture of 2-(2-tert-butoxycarbonylaminothiazol-4-yl)-4-methyl-2-pentenoic acid (1.56 g), diphenylmethyl 7β-amino-3-methylcarbamoyloxymethyl-3-cephem-4-carboxylate (2.27 g), and N-methylmorpholine (2.0 ml) in dichloromethane (50 ml) is added diphenylphosphoryl chloride (1.27 g) at −30° C. After 2 hours, the reaction mixture is neutralized with 10% citric acid, washed, dried, and purified by chromatography give diphenylmethyl 7β-[2-(2-tert-butoxycarbonylaminothiazol-4-yl)-4-methyl-2-pentenoylamino]-3-methylcarbamoyloxymethyl-3-cephem-4-carboxylate (2.27 g). Yield: 73%.

(16) In a mixture of ethyl acetate (8 to 30 parts), 1,2-dichloroethane (10 parts), N-methylmorpholine (1.5 equivalents), and the symmetric anhydride of carboxylic acid (3) (1.1 equivalents), heated under reflux for 10 minutes to 2 hours.

(17) In a mixture of chloroform (10 to 30 parts) and dimethoxyethane (10 parts), triethylamine (1.5 equivalents), and the mixed anhydride (2 equivalents) of carboxylic acid (3) and isobutoxyformic acid (1.5 equivalents), stirred at −5° C. to 10° C. for 30 minutes to 6 hours.

(18) In a mixture of dichloromethane (10 to 30 parts), pyridine (1.5 equivalents), and mixed anhydride of carboxylic acid (3) and methanesulfonic acd (1.1 equivalents), stirred under warming from −70° C. to room temperature for 1 to 3 hours. Yield: 90 to 95%.

(19) In a mixture of ethyl acetate (10 to 30 parts), pyridine (1.5 equivalents), and the mixed anhydride of carboxylic acid (3) and diethyl hydrogen phosphate (1.5 equivalents), stirred at 0° C. to 10° C. for 1 to 5 hours.

(20) In a mixture of ethyl acetate (10 to 30 parts), dichloromethane (10 to 30 parts), N-methylmorpholine (1 equivalent), and mixed anhydride of carboxylic acid (3) and dichlorophosphoric acid (1.1 equivalents), stirred at 0° C. to room temperature for 1 to 3 hours.

(21) In a mixtur of lutidine (1.5 equivalents), dichloromethane (10 to 30 parts), and the mixed anhydride of carboxylic acid (3) and monochlorophosphoric acid dimethylamide (1.1 to 2 equivalents), stirred at 0° C. to 30° C. for 1 to 4 hours.

(22) Amine (2) having carboxy at position 4 of the cephem ring is dissolved in water (10 to 30 parts) containing sodium hydrogen carbonate (2.5 equivalents). Carboxylic acid (3) chloride (1.1 equivalents) is dropwise added thereto. The mixture is kept at −5° C. to room temperature for 30 minutes to 2 hours.

(23) Amine (2) having carboxy at position 4 of the cephem ring is treated with trimethylsilyl chloride and triethylamine (1.2 equivalents each) in dichloromethane (10 to 30 parts), and then treated with pyridine (4 equivalents) and carboxylic acid (3) chloride (1.1 equivalents) at −30° C. for 30 minutes to 2 hours, and then the resulting silyl ester is hydrolyzed with acid.

(24) In a solution of picoline (4 equivalents) and carboxylic acid (3) chloride (1.2 equivalents) in dichloromethane (5 to 30 parts), stirred at −30° C. to 0° C. for 30 minutes to 2 hours.

(25) In a mixture of dimethylformamide (2 parts), ethyl acetate (10 to 30 parts), triethylamine (1.1 equivalents), and carboxylic acid (3) chloride (1.1 equivalents), stirred at 0° C. to 20° C. for 30 minutes to 3 hours.

(26) In a mixture of dichloromethane (20 to 50 parts), pyridine (3 equivalents), and benzotriazol-1-yl ester of carboxylic acid (3) (3 equivalents), stirred at 10° C. to 50° C. for 5 to 30 hours.

(27) In a mixture of dioxane (10 parts) and phthalimidoyl ester of carboxylic acid (3) (2 equivalents), stirred at 10° C. to 50° C. for 2 to 8 hours.

(28) In a mixture of methyl isobutyl ketone (10 to 30 parts) and succinimidoyl ester of carboxylic acid (3) (1.5 equivalents), stirred at 0° C. to 40° C. for 2 to 9 hours.

(29) In a manner similar to above, amides (I) on Tables 1 to 5 are prepared.

EXAMPLE 2

(Sodium Salt)

(1) To a solution of a carboxylic acid on Table 2 in acetone (10 to 30 parts) is added a solution of sodium ethylhexanoate (1 to 2 equivalents) in isobutanol. The mixture is diluted with ethyl acetate and ether. The separating crystals are collected by filtration to give the corresponding sodium salt.

(2) Similarly, to a suspension of a carboxylic acid on Table 3 (1 g) in water is added aqueous sodium carbonate to make a solution of pH 6.5. This is desalted, and poured into a 10 ml vial, and lyophylized to give a sodium salt preparation as above.

(3) The sodium salt (1 g) prepared under sterile condition is dissolved in sterile water (4 g) and given twice a day orally or intravenously to a patient suffering from *Staphylococcus aureus* infection for treating this disease. The minimal inhibitory concentration of this sodium salt determined by the standard method of Japan Society of Chemotherapy is 0.4 to 0.8 μg/ml against *Staphylococcus aureus* JC-1, 0.006 to 0.0125 μg/ml against *Streptococcus pyogenes* C-203, and 0.1 to 0.4 μg/ml against *Escherichia coli* H.

(4) In a manner similar to above, sodium salts (I) on Table 2 are prepared.

EXAMPLE 3

(Deprotection of Protected Carboxy)

(1) A solution of the corresponding diphenylmethyl ester in a mixture of dichloromethane (0 to 30 parts), trifluoroacetic acid (1 to 9 parts), and anisole (0.5 to 10 parts) is stirred under ice water cooling or at room temperature for 0.5 minutes to 5 hours. The solution is concentrated to remove the solvent and reagent. The residue is washed with a mixture of ether and hexane to give a carboxylic acid on Table 2 and 3 in 70 to 90% yield. When the starting material has tert-butoxycarbonylamido, this can also be removed to give the corresponding trifluoroacetate of the amino.

(2) To a solution of the corresponding diphenylmethyl ester in a mixture of dichloromethane (5 to 30 parts) and anisole (2 to 20 parts) is added aluminum chloride, tin tetrachloride, or titanium tetrachloride (3 to 12 equivalents) at −10° C. to 10° C., and the mixture is stirred at −10° C. to 40° C. for 1 to 24 hours. The mixture is washed with diluted hydrochloric acid and water, dried and concentrated to give a carboxylic acid on Table 3 in 80 to 90% yield. A tert-butoxycarbonylamino when present, is deprotected to give amino simultaneously.

(3) To a solution of the corresponding diphenylmethyl ester in anisole (2 to 10 parts) are added 90% formic acid (5 to 6 parts). The mixture is stirred at 50° C. to 60° C. for 1 to 4 hours to give a carboxylic acid on Table 2 in 40 to 50% yield.

EXAMPLE 4

(Esterification)

(1) (Acetoxymethyl ester) To a solution of the corresponding carboxylic acid potassium salt in N,N-dimethylformamide (2 to 10 parts) is added dropwise bromomethyl acetate (1 to 2 equivalents) at −10° C. to 20° C. After stirring for 15 minutes to 2 hours, the mixture is diluted with ethyl acetate, washed with ice water and aqueous sodium hydrogen carbonate, dried, and concentrated. The residue is crystallized from ethyl acetate to give an acetoxymethyl ester on Table 4. Yield: 60 to 70%.

(2) (1-Acetoxyethyl ester) To a solution of the corresponding carboxylic acid in N,N-dimethylformamide (2 to 10 parts) are added potassium carbonate (1 to 2 equivalents) and potassium fluoride (1 to 2 equivalents) at −15° C., and the mixture is stirred for 10 minutes. To the mixture is added dropwise bromoethyl acetate (3 equivalents) and the mixture is stirred at −15° to 0° C. for 1 to 2 hours. The reaction mixture is diluted with ice water and extracted with ethyl acetate. The extract is washed with water, dried, and concentrated under reduced pressure. The residue is purified by silica gel chromatography to give a 1-acetoxyethyl ester on Table 4. Yield: 40 to 70%.

(3) (Pivaloyloxymethyl ester) To a solution of the corresponding carboxylic acid potassium salt in N,N-dimethylformamide (2 to 10 parts) is added dropwise iodomethyl pivalate (1 to 2 equivalents) at −40° C. to 30° C. After stirring for 15 minutes to 4 hours, the mixture is diluted with ethyl acetate, washed with ice water and aqueous sodium hydrogen carbonate, dried, and concentrated under reduced pressure. The residue is purified by column chromatography to give a pivaloyloxymethyl ester on Table 4. Yield: 60 to 85%.

(4) (1-Pivaloyloxyethyl ester) To a solution of the corresponding carboxylic acid in N,N-dimethylformamide (5 to 10 parts) are added potassium carbonate (1 to 2 equivalents) at −30° C., and the mixture is stirred for 10 minutes. To the mixture is added dropwise 1-iodoethyl pivalate (1 to 3 equivalents) and the mixture is stirred at −15° to 0° C. for 1 to 2 hours. The reaction mixture is diluted with ice water and extracted with ethyl acetate. The extract is washed with water, dried, and concentrated under reduced pressure. The residue is purified by chromatography over silica gel to give a 1-(pivaloyloxy)ethyl ester on Table 4. Yield: 40 to 70%.

(5) (1-Ethoxycarbonyloxyethyl ester) To a solution of the corresponding carboxylic acid sodium salt in N,N-dimethylformamide (5 to 10 parts) is added dropwise 1-iodoethyl ethoxyformate (1 to 2 equivalents) at 0° C. After stirring at −15° C. to 0° C. for 1 to 2 hours, the mixture is diluted with ice water and extracted with ethyl acetate. The extract is washed with water, dried, and concentrated under reduced pressure. The residue is purified by chromatography over silica gel to give a 1-(ethoxycarbonyloxy)-ethyl ester in Table 4. Yield: 30 to 50%.

(6) (4-methyl-2-oxo-1,3-dioxol-5-ylmethyl ester) To a solution of the corresponding carboxylic acid sodium salt in N,N-dimethylformamide (5 to 10 parts) is added dropwise 5-bromomethyl-4-methyl-1,3-dioxol-2-one (1 to 2 equivalents). After stirring at −5° C. to 5° C. for 1 to 3 hours, the mixture is diluted with ice water and extracted with ethyl acetate. The extract is washed with water, dried, and concentrated under reduced pressure. The residue is purified by chromatography over silica gel to give a 4-methyl-2-oxo-1,3-dioxol-5-ylmethyl ester on Table 4. Yield: 40 to 60%.

(7) In a manner similar to above, other pharmacologically acceptable esters (I) on Table 4 {i.e., 1-(cyclohexylcarbonyloxy)-1-cyclohexylmethyl ester, 1-(cyclohexylmethoxycarbonyloxy)propyl ester, 1-(cyclohexyloxycarbonyloxy)ethyl ester, 1-(isopentenyloxycarbonyloxy)propyl ester, 1-(isopropoxycarbonyloxy)ethyl ester, 1-(isopropoxycarbonyloxy)propyl ester, and 1-(tert-butoxycarbonyloxy)ethyl ester} are prepared from the corresponding carboxylic acid using the same molar ratio of halide of the ester group.

(8) An amino-unprotected pharmacologically acceptable ester (100 mg), corn starch (150 mg), and magnesium stearate (5 mg) are granulated conventionally and filled in a capsule. This capsule (1 or 2 capsules, 2 to 3 times per day) is administered orally to treat an infection caused by *Staphylococcus aureus*.

(9) (Diphenylmethyl ester) To a solution of the corresponding carboxylic acid in a mixture of dichloromethane (10 parts) and methanol (10 parts) is added diphenyldiazomethane (1.2 equivalents). After stirring at room temperature for 1 hour, the mixture is washed with diluted hydrochloric acid and water, dried, and concentrated under reduced pressure. The residue is a diphenylmethyl ester on Table 1.

EXAMPLE 5

(Alkylcarbamoyl Ester Formation)

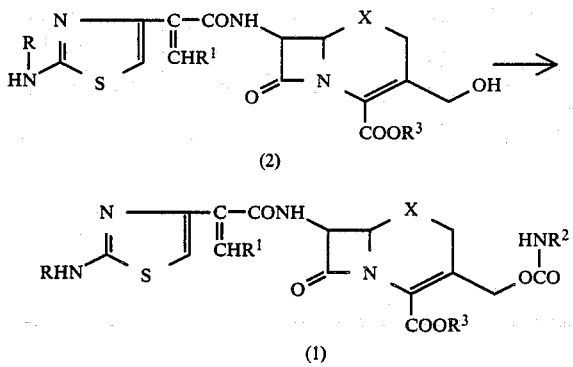

To a solution of the corresponding 3-hydroxymethyl-3-cephem-4-carboxylic acid sodium salt (2) in tetrahydrofuran (5 to 20 parts) are added alkyl isocyanate (3 to 10 equivalents) and pyridine (1 to 7 equivalents) or di-(tri-n-butylstannyl) oxide (0.05 to 1 equivalent) and the mixture is stirred for 1 to 5 hours. The reaction mixture is diluted with aqueous 5% sodium hydrogen carbonate and separating aqueous layer is taken. This is acidified to pH 3 with 10% hydrochloric acid and extracted with ethyl acetate. The extract is washed with water, dried, and concentrated. The residue is purified by column chromatography over silica gel to give a 3-N-alkylcarbamoyloxymethyl compound (1) on Table 2. Yield: 50 to 80%.

The produced acid may be dissolved by adding aqueous sodium hydrogen carbonate (1 equivalent) and lyophilized to give the corresponding sodium salt.

EXAMPLE 6

(Deprotection of Protected Amino)

(1) To a solution of the corresponding tert-butoxycarbonylamino compound in dichloromethane (0 to 20 parts) are added trifluoroacetic acid (0.3 to 20 parts) and anisole (0.5 to 10 parts), and the mixture is stirred at −10° C. to 40° C. for 10 minutes to 3 hours. The mixture is concentrated to remove the solvent and reagent and the resulting residue is washed with benzene or ether to give an amino compound on Table 3 or 5. Yield: 70 to 80%.

(2) To a solution of the corresponding tert-butoxycarbonylamino compound in dichloromethane (5 to 9 parts) are added anisole (2 to 8 parts) and aluminum chloride, titanium tetrachloride, or tin tetrachloride (3 to 12 equivalents), and the mixture is stirred at −10° C. to 10° C. for 1 to 24 hours. The mixture is extracted with hydrochloric acid. The extract is passed through a column of adsorbent, and concentrated to give an amino compound in Table 3 or 5. Yield: 60 to 80%.

EXAMPLE 7

(Reduction of Sulfoxide)

To a solution of the corresponding sulfoxide in dichloromethane (5 to 50 parts) is added phosphorus tribromide (1 to 3 equivalents) at −40° C. to −10° C. and the mixture is stirred for 30 minutes to 5 hours. The reaction mixture is diluted with dichloromethane, washed with aqueous sodium hydrogen carbonate and water, dried, and concentrated to give a sulfide.

EXAMPLE 8

(Sulfoxide Introduction)

To a solution of the corresponding sulfide in chloroform (10 to 20 parts) is added m-chloroperbenzoic acid (1 equivalent), and the mixture is stirred for 20 to 90 minutes. The reaction mixture is washed with aqueous sodium hydrogen carbonate, dired, and concentrated under reduced pressure to give a sulfoxide on Table 4. Yield: 60 to 80%.

PREPARATION 1

(1) To a solution of 2-(2-tert-butoxycarbonylamino-thiazol-4-yl)-2-hexenoic acid (2.064 g) in dichloromethane (30 ml) are added triethylamine (1.02 ml) and methanesulfonyl chloride (0.56 ml) at −65° C., and the mixture is stirred for 3 hours at −65° C. The reaction mixture is mixed with 7β-aminocephalosporanic acid (2.35 g), triethylamine (2.4 ml), and dichloromethane (40 ml), and stirred at −70° C. to −5° C. for 2 hours. The reaction mixture is acidified with 10% hydrochloric acid, washed with water, dried, and concentrated to give 7β-[2-(2-tert-butoxycarbonylaminothiazol-4-yl)-2-hexanoylamino]cephalosporanic acid (3.58 g). Yield: 95.5%.

(2) To a solution of 7β-[2-(2-tert-butoxycarbonylaminothiazol-4-yl)-2-hexenoylamino]cephalosporanic acid (3.58 g) in methanol (35 ml) is added dropwise aqueous 1N-sodium hydroxide (16 ml) at −30° C., and the mixture is stirred at −30° C. to −20° C. for 1 hour. The reaction mixture is acidified with 1N-hydrochloric acid (16 ml) and the separated crystals are collected to give 7β-[2-(2-tert-butoxycarbonylaminothiazol-4-yl)-2-hexenoylamino]-3-hydroxymethyl-3-cephem-4-carboxylic acid sodium salt (2.67 g). Yield: 77.2%.

IR (Nujol)ν: 3220, 1755, 1725, 1660, 1605, 1550.
NMR (CDCl₃—CD₃OD)δ: 0.95(t, J=8 Hz, 3H), 1.55 (s, 9H), 1.55(q, J=8 Hz, 2H), 2.35(brq, J=8 Hz, 2H), 3.52(brs, 2H), 3.82(brs, 2H), 5.03(d, J=5 Hz, 1H), 5.79(d, J=5 Hz, 1H), 6.44(t, J=8 Hz, 1H), 6.79 (s, 1H).

PREPARATION 2

(1) To a solution of 2-(2-tert-butoxycarbonylaminothiazol-4-yl)-4-methyl-2-pentenoic acid (4.48 g) in dichloromethane (60 ml) are added triethylamine (2.2 ml) and methanesulfonyl chloride (1.23 ml) at −65° C., and the mixture is stirred for 3 hours. The reaction mixture is mixed with 7β-aminocephalosporanic acid (5.1 g), triethylamine (5.2 ml), and dichloromethane (100 ml) and stirred at −70° C. to −5° C. for 2 hours. The reaction mixture is acidified with 10% hydrochloric acid, washed with water, dried, and concentrated to give 7β-[2-(2-tert-butoxycarbonylaminothiazol-4-yl)-4-methyl-2-pentenoylamino]cephalosporanic acid (5.12 g). Yield: 62.9%.

IR (Nujol)ν: 3400, 1780, 1720, 1670, 1600.
NMR (CDCl₃—CD₃OD)δ: 1.05(d, J=7 Hz, 6H), 1.52 (s, 9H), 2.04(s, 3H), 2.73∼3.13(m, 1H), 3.4(m, 2H), 4.91, 5.13(ABq, J=13 Hz, 2H), 5.09(d, J=5 Hz, 1H), 5.86(d, J=5 Hz, 1H), 6.22(d, J=10 Hz, 1H), 6.78 (s, 1H).

(2) To a solution of 7β-[2-(2-tert-butoxycarbonylaminothiazol-4-yl)-4-methyl-2-pentenoylamino]cephalosporanic acid (5.12 g) in methanol (50 ml) is added dropwise aqueous 1N-sodium hydroxide (22.6 ml) at −30° C., and the mixture is stirred at −30° C. to −20° C. for 1 hour. The reaction mixture is acidified with 1N-hydrochloric acid (22.6 ml) and the separating crystals are collected to give 7β-[2-(2-tert-butoxycarbonylaminothiazol-4-yl)-4-methyl-2-pentenoylamino]-3-hydroxymethyl-3-cephem-4-carboxylic acid sodium salt (2.67 g). Yield: 77.2%.

IR (Nujol)ν: 3250, 1755, 1725, 1660, 1600.
NMR (CDCl₃—CD₃OD)δ: 1.06(d, J=7 Hz,, 6H), 1.53 (s, 9H), 2.5∼3.1(m, 1H), 3.4(m, 2H), 3.81(s, 2H), 5.02(d, J=5 Hz, 1H), 5.77(d, J=5 Hz, 1H), 6.22(d, J=10 Hz, 1H), 6.80(s, 1H).

TABLE 1

PHYSICAL CONSTANTS OF THE PRODUCTS

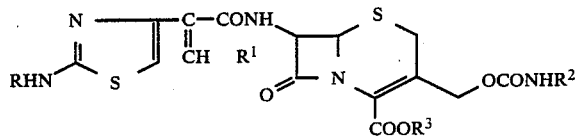

| No. | R | $R^1$ | $R^2$ | $R^3$ | IR(CHCl₃)ν:cm⁻¹ | Protected Compound NMR(CDCl₃) δ :ppm | Ex. No. |
|---|---|---|---|---|---|---|---|
| 1 | BOC | Me | Me | BH | nd | 1.51(s, 9H), 2.08(d, J=7Hz, 3H), 2.67(d, J=4Hz, 3H), 3.23(brs, 2H), 4.77, 5.06(ABq, J=14Hz, 2H), 4.9(m, 1H), 4.94(d, J=4Hz, 1H), 5.73(dd, J=4Hz, J=9Hz, 1H), 6.50(q, J=7Hz, 1H), 6.62(s, 1H), 6.80(s, 1H), 7.1∼7.5 (m, 10H), 8.03(d, J=9Hz, 1H). | (4-9) |
| 2 | BOC trans | Me | Me | BH | 1772, 1718, 1662, 1146. | 1.53(s, 9H), 1.91(d, J=7.5Hz, 3H), 2.68(d, J=5.0Hz, 3H), 3.15 (s, 2H), 4.82(d, J=4.5Hz, 1H), 4.76, 5.02(ABq, J=14.4Hz, 2H), 5.56(dd, J=4.5Hz, J=8.0Hz, 1H), 6.51(s,1H), 6.72(s, 1H), 7.21∼7.40(m, 12H), 7.97(d, J=8.0Hz, 1H). | (4-9) |
| 3 | BOC | Et | Me | BH | 3450, 3400, 2950, 1775, 1715, 1665, 1150. | 1.10(t, J=8Hz, 3H), 1.52(s, 9H), 2.56(quintet, J=8 Hz, 2H), 2.70(d, J=5Hz, 3H), 3.25 (brs, 2H), 4.80, 5.06 (ABq, J=14Hz, 2H), 4.98(d, J=5Hz, 1H), 5.75 | (4-9) (1-14) |

TABLE 1-continued
PHYSICAL CONSTANTS OF THE PRODUCTS

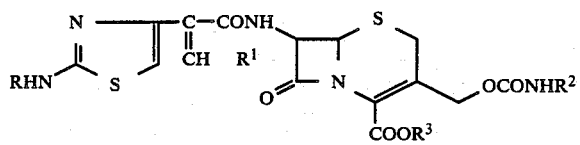

| No. | R | $R^1$ | $R^2$ | $R^3$ | IR(CHCl$_3$)$\nu$:cm$^{-1}$ | NMR(CDCl$_3$) $\delta$ :ppm | Ex. No. |
|---|---|---|---|---|---|---|---|
| | | | | | | (dd, J=5Hz, J=9Hz, 1H), 6.42(t, J=(Hz, 1H), 6.70(s, 1H, 6.85(s, 1H), 7.30~7.40(m, 10H), 7.86(d, J=9Hz, 1H), 9.60(brs,1H). | |
| 4 | BOC | Et | Et | BH | nd | 1.07(t, J=8Hz, 3H), 1.10(t, J=8Hz, 3H), 1.52(s, 9H), 2.54 (quintet, J=8Hz, 2H), 3.12(quintet, J=8Hz, 2H), 3.22(brs, 2H), 4.80(brs, 1H), 4.78, 5.01(ABq, J=14Hz, 2H), 4.95(d, J=5 Hz, 1H), 5.70(dd, J=5Hz, J=8Hz, 1H), 6.40(t, J=8Hz, 1H), 6.68 (s, 1H), 6.82(s, 1H), 7.20~7.42 (m, 10H), 7.84(d, J=8Hz, 1H). | (4-9) |
| 5 | BOC | n-Pr | Me | BH | 3450, 3400, 1785, 1725, 1670. | 0.97(t, J=7Hz, 3H), 1.51(brq, J=7Hz, 2H), 1.53(s, 9H), 2.53(q, J=7Hz, 2H), 2.68(d, J=5Hz, 3H), 3.23(brs, 2H), 4.79, 5.04(ABq, J=13Hz, 2H), 4.97(d, J=5Hz, 1H), 5.71(dd, J=5Hz, J=8Hz, 1H), 6.42(t, J=7Hz, 1H), 6.67(s, 1H), 6.83(s, 1H), 7.33(m, 10H), 7.89(d, J=8Hz, 1H). | (4-9) |
| 6 | BOC | i-Pr | Me | BH | 3450, 3400, 1780, 1720, 1670. | 1.08(d, J=7Hz, 6H), 1.52(s, 9H), 2.65(d, J=5Hz, 3H), 2.9~3.4 (m, 1H), 3.21(brs, 2H), 4.78, 5.00(ABq,, J=14 Hz, 2H), 4.96(d, J=5Hz, 1H), 5.71(dd, J=5Hz, J=8Hz, 1H), 6.22(d, J=10Hz, 1H), 6.71(s, 1H), 6.84(s, 1H), 7.3(m, 10H), 7.70(d, J=8Hz, 1H). | (1-15) (4-9) |

TABLE 2

| No. | R | $R^1$ | $R^2$ | $R^3$ | IR(CHCl$_3$)$\nu$: cm$^{-1}$ | NMR(CDCl$_3$) $\delta$: ppm | Ex. No. |
|---|---|---|---|---|---|---|---|
| | | | | | | N—Protected carboxy compound and its salts | |
| | | | | | | (Part 1) | |
| 1 | BOC | Me | Me | H | nd | 1.54(s, 9H), 1.98(d, J=7Hz, 3H), 2.72(s, 3H), 3.45, 3.66(ABq, J=18Hz, 2H), 4.92, 5.11(ABq, J=12Hz, 2H), 5.03(d, J=4Hz, 1H), 5.83(d, J=4Hz, 1H), 6.50(q, J=7Hz, 1H), 6.81(s, 1H). [CDCl$_3$—CD$_3$OD] | (3-1) (5-1) |
| 2 | BOC trans | Me | Me | Na | nd | 2.29(d, J=7.5Hz, 3H), 3.12(s, 3H), 3.56~4.12(m, 2H), 4.23(s, 2H), 5.52(d, J=4.5Hz, 1H), 6.12(d, J=4.5Hz, 1H), 7.41(s, 1H), 7.45(q, J=7.5Hz, 1H).[D$_2$O/TMS external standard] | (2-1) (5-1) |
| 3 | BOC | Et | Me | H | 3450, 3400, 1780, 1720, 1670, 1540, 1365, 1150. | 1.08(t, J=8Hz, 3H), 1.54(s, 9H), 2.42(quintet, J=8 Hz, 2H), 2.74(s, 3H), 3.40, 3.57(ABq, J=18Hz, 2H), 4.85, 5.07(ABq, J=13Hz, 2H), 5.05(d, J=5Hz, 1H), 5.83(d, J=5Hz, 1H), 6.40(t, J=8Hz, 1H), 6.76(s, 1H). [CDCl$_3$—CD$_3$OD] | (5-1) |
| 4 | BOC | Et | Me | Na | 3400, 1760, 1710, 1655, 1603, 1540. [KBr] | 1.08(t, J=7Hz, 3H), 1.53(s, 9H), 2.30(quintet, J=7 Hz, 2H), 2.68(s, 3H), 3.33, 3.56(ABq, J=17Hz, 2H), 4.74, 4.88(ABq, J=6Hz, 2H), 5.07(d, J=5Hz, 1H), 5.76(d, J=5Hz, 1H), 6.49(t, J=7Hz, 1H), 6.79(s, 1H) [CD$_3$OD]. | (2-1) (5-1) |
| | | | | | | (Part 2) | |
| 5 | BOC | Et | Et | H | nd | 1.08(t, J=8Hz, 3H), 1.12(t, J=8Hz, 3H), 1.53(s, 9H), 2.42(quintet, J=8Hz, 2H), 3.15(q, J=8Hz, 2H), 3.40, 3.56(ABq, J=21Hz, 2H), 4.86, 5.07(ABq, J=13Hz, 2H), 5.05(d, J=5Hz, 1H), 5.83 (d, J=5Hz, 1H), 6.40(t, J=8Hz, 1H), 6.76(s, 1H). [CDCl$_3$—CD$_3$OD] | (3-1) (5-1) |
| 6 | BOC | Et | i-Pr | Na | 3330, 1765, 1720, 1655, 1615, 1540. [Nujol] | 1.05(t, J=7Hz, 3H), 1.13(d, J=7Hz, 6H), 1.53(s, 9H), 230(quintet, J=7Hz, 2H), 3.35, 3.54(ABq, J=11Hz, 2H), 3.7(m, 1H), 4.74, 4.86(ABq, J=6Hz, 2H), 5.07(d, J=4Hz, 1H), 5.77(d, J=4Hz, 1H), 6.50(t, J=7Hz, 1H), 6.78(s, 1H). [CD$_3$OD] | (2-1) (5-1) |
| 7 | BOC | n-Pr | Me | H | 3230, 1780, 1720, 1660. [Nujol] | 0.95(t, J=8Hz, 3H), 1.40~1.63(m, 2H), 1.54(s, 9H), 2.22~2.47 (m, 2H), 2.72(s, 3H), 3.51(m, 2H), 4.84, 5.12(ABq, J=15Hz, 2H), 5.09(d, J=5Hz, 1H), 5.84(d, J=5Hz, 1H), 6.45(t, J=8Hz, 1H), 6.87(s, 1H). [CDCl$_3$—CD$_3$OD] | (3-1) (5-1) |
| 8 | BOC | i-Pr | Me | H | nd | nd  This product was subjected to the treatment of next step without isolation. | (3-1) (5-1) |

TABLE 3

Carboxy compound and its salts

| No. | R | R¹ | R² | R³ | IR(CHCl₃)ν: cm⁻¹ | NMR(CDCl₃) δ: ppm | Ex. No. |
|---|---|---|---|---|---|---|---|
| | | | | | (Part 1) | | |
| 1 | H TFA | Me | Me | H | 3300, 1700, 1705, 1660, 1528. [KBr] | 1.92(d, J=7Hz, 3H), 2.68(s, 3H), 3.47, 3.63(ABq, J=17Hz, 2H), 4.75, 5.09(ABq, J=12Hz, 2H), 5.11(d, J=4Hz, 1H), 5.82(d, J=4Hz, 1H), 6.43(q, J=7Hz, 1H), 6.48(s, 1H). [CD₃OD] | (6-1) |
| 2 | H TFA trans | Me | Me | H | 1772, 1702sh, 1663. [Nujol] | 2.23(d, J=7Hz, 3H), 2.88(d, J=6.5Hz, 3H), 3.86(brs, 2H), 4.99, 5.28(ABq, J=12.6Hz, 2H), 5.45(d, J=4.5Hz, 1H), 6.11(d, J=4.5 1H), 6.94(s, 1H), 7.22q | (3-1) (6-1) |
| | | | | | (Part 2) | | |
| 5 | H TFA | Et | i-Pr | H | 3300, 1772, 1650br, 1530. [KBr] | 1.08(t, J=7Hz, 3H), 1.13(d, J=7Hz, 6H), 2.34(quintet, J=7Hz, 2H), 3.51, 3.68(ABq, J=21Hz, 2H), 3.7(m, 1H), 4.81, 5.12(ABq, J=12Hz, 2H), 5.17(d, J=5Hz, 1H), 5.84(d, J=5Hz, 1H), 6.37(t, J=7Hz, 1H), 6.68(s, 1H). [CD₃OD] | (6-1) |
| 6 | H | n-Pr | Me | H | 3300, 3250, 1780, 1755, 1695, 1660, 1635. [Nujol] | 0.97(brt, J=7Hz, 3H), 1.53(brq, J=7Hz, 2H), 2.35 (brq, J=7Hz, 2H), 2.73(s, 3H), 3.48, 3.62(ABq, J=18Hz, 2H), 4.88, 5.16(ABq, J=12Hz, 2H), 5.13(d, J=5Hz, 1H), 5.83(d, J=5Hz, 1H), 6.41(t, J=7Hz, 1H), 6.46(s, 1H). [CDCl₃—CD₃OD] | (3-1) (6-1) |
| 7 | H | i-Pr | Me | H | 3280, 1765, 1700, 1655, 1635. [Nujol] | 1.10(d, J=7Hz, 6H), 2.50~2.95(m, 1H), 2.74(s, 3H), 3.30~3.80 (m, 2H), 4.91, 5.13(ABq, J=13Hz, 2H), 5.11(d, J=5Hz, 1H), 5.85 (d, J=5Hz, 1H), 6.21(d, J=10Hz, 1H), 6.42(s, 1H). [CDCl₃—CD₃OD] | (3-1) (6-1) |

TABLE 4

N—Protected pharmacologically acceptable ester

| No. | R | R¹ | R² | R³ | IR(CHCl₃)ν: cm⁻¹ | NMR(CDCl₃) δ: ppm | Ex. No. |
|---|---|---|---|---|---|---|---|
| | | | | | (Part 1) | | |
| 1 | BOC | Me | Me | AOM | 3445, 3400, 1785, 1722, 1677, 1540. | 1.52(s, 9H), 1.97(d, J=7Hz, 3H), 2.09(s, 3H), 2.75 (d, J=5Hz, 3H), 3.48(s, 2H), 4.76, 5.07(ABq, J=18Hz, 2H), 5.00(d, J=4Hz, 1H), 5.36(m, 1H), 5.82(s, 2H), 5.91(m, 1H), 6.46(q, J=7Hz, 1H), 6.75(s, 1H), 7.99 (d, J=9Hz, 1H), 9.50(brs, 1H). | (4-1) |
| 2 | BOC | Me | Me | AOE | 3440, 1782, 1753, 1720, 1672. | 1.46~1.60(m, 3H), 1.52(s, 9H), 2.00(d, J=7Hz, 3H), 2.07(s, 3H), 2.76(d, J=5Hz, 3H), 3.33, 3.57(ABq, J=18Hz, 2H), 4.78, 5.10(ABq, J=13Hz, 2H), 5.01(d, J=4 Hz, 1H), 5.60~5.95(m, 2H), 6.23(s, 1H), 6.47(q, J=7Hz, 1H), 7.88(d, J=9Hz, 1H), 8.21(brs, 1H). | (4-2) |
| 3 | BOC | Me | Me | POM | 3450, 3400, 1780, 1745sh, 1720, 1670, 1540. | 1.20(s, 9H), 1.51(s, 9H), 2.01(d, J=7Hz, 3H), 2.76 (d, J=5Hz, 3H), 3.42, 3.51(ABq, J=17Hz, 2H), 4.79, 5.06(ABq, J=16Hz, 2H), 5.03(d, J=4Hz, 1H), 5.19(q, J=5Hz, 1H), 5.86(s, 2H), 5.8(m, 1H), 6.52(q, J=7Hz, 1H), 6.72(s, 1H), 8.02(d, J=7Hz, 1H), 9.87 (br, 1H). | (4-3) |
| | | | | | (Part 2) | | |
| 4 | BOC | Me | Me | HOH | 3460, 1785, 1740, 1720, 1675, 1542. | 1.00~2.0(m, 21H), 2.02(d, J=7Hz, 3H), 2.2~2.4(m, 1H), 2.75(d, J=5Hz, 3H), 3.42, 3.51(ABq, J=18Hz, 2H), 4.78, 5.05(ABq, J=16Hz, 2H), 5.02(d, J=4.5Hz, 1H), 5.20(q, J=5Hz, 1H), 5.8(m, 1H), 6.51(d, J=7Hz, 1H), 6.52(q, J=7Hz, 1H), 6.71(s, 1H), 8.02(d, J=7Hz, 1H), 9.87(brs, 1H). | (4-7) |
| 5 | BOC | Me | Me | ECE | 3410, 1785, 1761, 1720, 1675, 1150. | 1.29(t, J=7Hz, 3H), 1.52(s, 9H), 1.54~1.66(m, 3H), 1.99(d, J=8Hz, 3H), 2.76(d, J=5Hz, 3H), 3.34, 3.63 (ABq, J=18Hz, 2H), 4.21(q, J=7Hz, 2H), 4.75, 5.03 (ABq, J=13Hz, 2H), 5.00(d, J=4Hz, 1H), 5.60~6.03(m, 2H), 6.41(t, J=8Hz, 1H), 6.45(s, 1H), 8.20(d, J=9Hz, 1H), 9.13(brs, 1H). | (4-5) |
| 6 | BOC | Me | Me | ICE | 3440, 3380, 1780, 1755, 1720, 1678. | 1.30(d, J=6Hz, 6H), 1.53(s, 9H), 1.50~1.61(m, 3H), 2.01(d, J=8Hz, 3H), 2.78(d, J=5Hz, 3H), 3.41, 3.61 (ABq, J=18Hz, 2H), 4.65~5.21(m, 2H), 5.15(d, J=5Hz, 1H), 5.33(q, J=5Hz, 1H), 5.79(dd, J=5Hz, J=9Hz, 1H), 6.45(q, J=8Hz, 1H), 6.71(m, 1H), 6.75(s, 1H), 6.82 (m, 1H), 7.70(d, J=9Hz, 1H), 7.86(brs, 1H). | (4-7) |
| | | | | | (Part 3) | | |
| 7 | BOC | Me | Me | HCE | 3450, 3400, 1780, 1760, 1718, 1665, 1540, 1150. | 1.0~2.0(m, 10H), 1.51(s, 9H), 1.52(d, J=6Hz, 3H), 2.08(d, J=8Hz, 3H), 2.78(d, J=5Hz, 3H), 3.40, 3.60 (ABq, J=18Hz, 2H), 4.4~5.3(m, 3H), 5.02(d, J=4.5Hz, 1H), 5.26(dd, J=4.5Hz, J=8Hz, 1H), 5.28(q, J=5Hz, 1H), 6.62(q, J=8Hz, 1H), 6.73(s, 1H), 6.85(q, J=6Hz, 1H), 7.96(brs, 1H), 8.01(d, J=8Hz, 1H). | (4-7) |
| 8 | BOC | Et | Me | AOM | 3450, 3400, 1780, 1720, 1675, 1540. | 1.06(t, J=7Hz, 3H), 1.52(s, 9H), 2.09(s, 3H), 2.4(m, 2H), 2.72 (d, J=5Hz, 3H), 3.46(s, 2H), 4.75, 5.07 (ABq, J=14Hz, 2H), 4.98(d, J=4Hz, 1H), 5.35(m, 1H), 5.8(m, 1H), 5.82(s, 2H), 6.41(t, J=7Hz, 1H), 6.74 (s, 1H), 7.98(d, J=9Hz, 1H), 9.87(brs, 1H). | (4-1) |
| 9 | BOC | Et | Me | AOE | 1780, 1755, 1721, 1668. | 1.07(t, J=7Hz, 3H), 1.52(s, 9H), 1.45~1.60(m, 3H), 2.07(s, 3H), 2.30~2.66(m, 2H), 2.75(d, J=4Hz, 3H), | (4-2) (7-1) |

TABLE 4-continued

| | | | | | N—Protected pharmacologically acceptable ester | | |
|---|---|---|---|---|---|---|---|
| No. | R | R¹ | R² | R³ | IR(CHCl₃)ν: cm⁻¹ | NMR(CDCl₃) δ: ppm | Ex. No. |
| | | | | | | 3.33, 3.56(ABq, J=18Hz, 2H), 4.77, 5.10(ABq, J=14Hz, 2H), 4.99(d, J=4Hz, 1H), 5.60~5.97(m, 1H), 6.41(t, J=7Hz, 1H), 6.23(s, 1H), 6.80~7.20(m, 1H), 7.85(d, J=9Hz, 1H). | |
| | | | | | (Part 4) | | |
| 10 | BOC | Et | Me | AOE SO | 1796, 1752, 1720, 1663. | 1.09(t, J=7Hz, 3H), 1.52(s, 9H), 1.53(d, J=6Hz, 3H), 2.09(s, 3H), 2.33~2.77(m, 2H), 2.76(d, J=5Hz, 3H), 3.32, 3.92(ABq, J=18Hz, 2H), 4.60(d, J=4Hz, 1H), 4.73, 5.23(ABq, J=14Hz, 2H), 6.18, 6.29(dd, J=4Hz, 1H), 6.46(t, J=7Hz, 1H), 6.76(s, 1H), 6.29~7.23(m, 1H), 8.80(d, J=9Hz, 1H). | (8-1) |
| 11 | BOC | Et | Me | POM | 3450, 3400, 1780, 1750, 1720, 1665, 1540, 1365, 1150. | 1.07(t, J=8Hz, 3H), 1.22(s, 9H), 1.53(s, 9H), 2.46(quintet, J=8Hz, 2H), 2.75(d, J=5Hz, 3H), 3.41, 3.52(ABq, J=18Hz, 2H), 4.75~4.95(m, 1H), 4.77, 5.03(ABq, J=14Hz, 2H), 5.01(d, J=5Hz, 1H), 5.88(dd, J=5Hz, J=8Hz, 1H), 5.84, 5.92(ABq, J=6Hz, 2H), 6.42(t, J=8Hz, 1H), 6.74(s, 1H), 7.67(d, J=8Hz, 1H). | (4-3) |
| 12 | BOC | Et | Me | POE | 1785, 1745sh, 1730, 1672. | 1.08(t, J=7Hz, 3H), 1.20(s, 9H), 1.52(s, 9H), 1.53(d, J=6Hz, 3H), 2.27~2.67(m, 2H), 2.78(d, J=5Hz, 3H), 3.33, 3.62(ABq, J=18Hz, 2H), 4.78, 5.12(ABq, J=14Hz, 2H), 5.05(d, J=4Hz, 1H), 5.67~6.03(m, 1H), 6.43(t, J=7Hz, 1H), 6.75(s, 1H), 6.80~7.20(m, 1H), 7.23~7.96(m, 1H). | (4-4) |
| | | | | | (Part 5) | | |
| 13 | BOC | Et | Me | ECE | 1783, 1760, 1722, 1670. | 1.07(t, J=7Hz, 3H), 1.30(t, J=7Hz, 3H), 1.53(s, 9H), 1.53~1.66(m, 3H), 2.15~2.30(m, 2H), 2.76(d, J=5Hz, 3H), 3.33, 3.61(ABq, J=18Hz, 2H), 4.21(q, J=7Hz, 2H), 4.77, 5.10(ABq, J=14Hz, 2H), 4.99(d, J=4Hz, 1H), 5.60~6.03(m, 1H), 6.41(t, J=7Hz, 1H), 6.70~7.10(m, 1H), 7.15~7.85(m, 1H). | (4-5) (7-1) |
| 14 | BOC | Et | Me | ECE SO | 1800, 1760, 1722, 1668. | 1.08(t, J=7Hz, 3H), 1.31(t, J=6Hz, 3H), 1.52(s, 9H), 1.60(d, J=6Hz, 2H), 2.30~2.70(m, 2H), 2.75(d, J=5Hz, 3H), 3.32, 3.92(ABq, J=18Hz, 2H), 4.27(q, J=6Hz, 2H), 4.68(d, J=4Hz, 1H), 4.78, 5.22(ABq, J=13Hz, 2H), 6.23(q, J=4Hz, 1H), 6.48(t, J=7Hz, J=9Hz, 1H), 6.76(s, 1H), 6.83~7.20(m, 1H), 8.68(d, J=9Hz, 1H). | (8-1) |
| 15 | BOC | Et | Me | ICP | 3445, 3400, 1778, 1755, 1720, 1673. | 0.94(t, J=7Hz, 3H), 1.07(t, J=8Hz, 3H), 1.30(d, J=6Hz, 6H), 1.53(s, 9H), 1.6~2.1(m, 2H), 2.45(dq, J=8Hz, J=8Hz, 2H), 2.77(d, J=5Hz, 3H), 3.40, 3.59(ABq, J=18Hz, 2H), 4.65~5.30(m, 2H), 5.15(d, J=5Hz, 1H), 5.32(q, J=5Hz, 1H), 5.79(dd, J=5Hz, J=9Hz, 1H), 6.44(t, J=8Hz, 1H), 6.70(m, 1H), 6.75(s, 1H), 6.83(t, J=7Hz, 1H), 7.70(d, J=9Hz, 1H), 7.86(brs, 1H). | (4-7) |
| | | | | | (Part 6) | | |
| 16 | BOC | Et | Me | PeCP | 3440, 3390, 1780, 1753, 1720, 1670, 1150. | 0.93(t, J=7Hz, 3H), 0.95(t, J=7Hz, 3H), 1.0~2.0(m, 6H), 1.06(t, J=7Hz, 3H), 1.21(d, J=6Hz, 3H), 1.52(s, 9H), 2.4(m, 2H), 2.77(d, J=5Hz, 3H), 3.46(s, 2H), 4.80, 5.00(ABq, J=15Hz, 2H), 4.8(m, 1H), 4.98(d, J=4Hz, 1H), 5.28(q, J=5Hz, 1H), 5.35(m, 1H), 6.23(m, 1H), 6.41(t, J=7Hz, 1H), 6.74(s, 1H), 7.99(d, J=9Hz, 1H), 9.87(brs, 1H). | (4-7) |
| 17 | BOC | Et | Me | DOL | 3450, 3400, 1818, 1782, 1722, 1670, 1540. | 1.17(t, J=7Hz, 3H), 1.52(s, 9H), 2.18(s, 3H), 2.45(quintet, J=7Hz, 2H), 2.75(d, J=5Hz, 3H), 3.41, 3.58(ABq, J=19Hz, 2H), 4.74, 5.09(ABq, J=14Hz, 2H), 4.99(s, 2H), 5.03(d, J=4Hz, 1H), 5.1(m, 1H), 5.87(dd, J=4Hz, J=9Hz, 1H), 6.43(t, J=7Hz, 1H), 6.78(s, 1H), 7.81(d, J=9Hz, 1H), 9.56(brs, 1H). | (4-6) |
| 18 | BOC | Et | Et | POM | 3450, 3420, 2970, 2940, 1790, 1750, 1725, 1680, 1545, 1510, 1375, 1150. | 1.07(t, J=8Hz, 3H), 1.12(t, J=7Hz, 3H), 1.23(s, 9H), 1.53(s, 9H), 2.46(quintet, J=8Hz, 2H), 4.18(quintet, J=7Hz, 2H), 3.40, 3.53(ABq, J=18Hz, 2H), 4.35(brs, 1H), 4.78, 5.05(ABq, J=14Hz, 2H), 5.01(d, J=5Hz, 1H), 5.86(dd, J=5Hz, J=9Hz, 1H), 5.86(s, 2H), 6.42(t, J=8Hz, 1H), 6.75(s, 1H), 7.74(d, J=9Hz, 1H), 8.71 (brs, 1H). | (4-3) |
| | | | | | (Part 7) | | |
| 19 | BOC | Et | i-Pr | POM | 3400, 3200, 1792, 1745, 1720, 1670, 1540. | 1.08(t, J=7Hz, 3H), 1.15(d, J=7Hz, 6H), 1.23(s, 9H), 1.53(s, 9H), 2.47(quintet, J=7Hz, 2H), 3.40, 3.52(ABq, J=16Hz, 2H), 3.7(m, 1H), 4.76, 5.07(ABq, J=14Hz, 2H), 4.80(d, J=7Hz, 1H), 5.00(d, J=4Hz, 1H), 5.86(s, 2H), 5.87(dd, J=4Hz, J=9Hz, 1H), 6.42(t, J=7Hz, 1H), 6.74(s, 1H), 7.86(d, J=9Hz, 1H), 9.23(brs, 1H). | (4-3) |
| 20 | BOC | Et | i-Pr | HmCP | 3410, 3200, 1793, 1745, 1722, 1675, 1540. | 0.95(t, J=7Hz, 3H), 0.9~2.1(m, 13H), 1.08(t, J=7Hz, 3H), 1.15(d, J=7Hz, 6H), 1.53(s, 9H), 2.47(quintet, J=7Hz, 2H), 3.40, 3.52(ABq, J=16Hz, 2H), 3.54(m, 2H), 3.7(m, 1H), 4.76, 5.07(ABq, J=14Hz, 2H), 5.00(d, J=4Hz, 1H), 5.87(dd, J=4Hz, J=9Hz, 1H), 6.42(t, J=7Hz, 1H), 6.72(t, J=5Hz, 1H), 6.74(s, 1H), 7.86(d, J=9Hz, 1H), 9.23(brs, 1H). | (4-7) |

TABLE 4-continued

| | | | | | N—Protected pharmacologically acceptable ester | | |
|---|---|---|---|---|---|---|---|
| No. | R | $R^1$ | $R^2$ | $R^3$ | IR(CHCl$_3$)ν: cm$^{-1}$ | NMR(CDCl$_3$) δ: ppm | Ex. No. |
| | | | | | (Part 8) | | |
| 21 | BOC | n-Pr | Me | POM | 3450, 3400, 1785, 1745, 1720, 1670. | 0.93(t, J=7Hz, 3H), 1.21(s, 9H), 1.50(brq, 2H), 1.52(s, 9H), 2.42(brq, J=7Hz, 2H), 2.77(d, J=5Hz, 3H), 3.43, 3.55(ABq, J=18Hz, 2H), 4.78, 5.07(ABq, J=13Hz, 2H), 5.02(d, J=5Hz, 1H), 5.87 (s, 2H), 5.88(dd, J=5Hz, J=8Hz, 1H), 6.44(t, J=8Hz, 1H), 6.76 (s, 1H), 7.82(d, J=8Hz, 1H). | (4-3) |
| 22 | BOC | i-Pr | Me | POM | 3450, 3400, 1785, 1750, 1720, 1670. | 1.05(d, J=7Hz, 6H), 1.22(s, 9H), 1.52(s, 9H), 2.77 (d, J=5Hz, 3H), 2.83~3.22(m, 1H), 3.44, 3.58(ABq, J=18Hz, 2H), 4.79, 5.10(ABq, J=14Hz, 2H), 5.03(d, J=5Hz, 1H), 5.87(s, 2H), 5.90(dd, J=5Hz, J=8Hz, 1H), 6.25(d, J=10Hz, 1H), 6.77(s, 1H), 7.75(d, J=8Hz, 1H). | (4-3) |

TABLE 5

| | | | | | Pharmacologically acceptable ester | | |
|---|---|---|---|---|---|---|---|
| No. | R | $R^1$ | $R^2$ | $R^3$ | IR(CHCl$_3$)ν: cm$^{-1}$ | NMR(CDCl$_3$) δ: ppm | Ex. No. |
| | | | | | (Part 1) | | |
| 1 | H | Me | Me | AOM | 3425, 1782, 1728, 1695, 1660, 1540. [Nujol] | 1.89(t, J=7Hz, 3H), 2.08(s, 3H), 2.57(d, J=6Hz, 3H), 3.61(s, 2H), 4.61, 4.92(ABq, J=13Hz, 2H), 5.21(d, J=4Hz, 1H), 5.78(dd, J=4Hz, J=9Hz, 1H), 5.84(s, 2H), 6.23(s, 1H), 6.41(q, J=7Hz, 1H), 6.98(brs, 2H), 9.22 (d, J=9Hz, 1H). [CD$_3$SOCD$_3$] | (6-1) |
| 2 | H | Me | Me | AOE | 3380, 1778, 1751, 1723, 1670. | 1.54(d, J=6Hz, 3H), 1.88(d, J=7Hz, 3H), 2.10(s, 3H), 2.77(d, J=5Hz, 3H), 3.33, 3.56(ABq, J=19Hz, 2H), 4.78, 4.92(ABq, J=13Hz, 2H), 5.03(d, J=4Hz, 1H), 5.23(q, J=5Hz, 1H), 5.60(brs, 2H), 5.95(dd, J=4Hz, J=9Hz, 1H), 6.34(s, 1H), 6.41(q, J=7Hz, 1H), 6.92~7.25(m, 1H), 8.05(d, J=9Hz, 1H). | (6-1) |
| 3 | H | Me | Me | POM | 3480, 3400, 1787, 1750, 1730, 1670, 1520. | 1.21(s, 9H), 1.87(d, J=7Hz, 3H), 2.75(d, J=5Hz, 3H), 3.42, 3.54(ABq, J=18Hz, 2H), 4.77, 5.07(ABq, J=15 Hz, 2H), 5.04(d, J=4Hz, 1H), 5.2(m, 1H), 5.67(brs, 2H), 5.85, 5.91(ABq, J=6Hz, 2H), 5.9 (m, 1H), 6.21 (s, 1H), 6.48(q, J=7Hz, 1H), 8.62(d, J=9Hz, 1H). | (6-1) |
| | | | | | (Part 2) | | |
| 4 | H | Me | Me | HOH | 3410, 1780, 1745, 1672, 1515. | 0.97~1.98(m, 21H), 1.88(d, J=7Hz, 3H), 2.3~2.5(m, 1H), 2.75(d, J=5Hz, 3H), 3.43, 3.55(ABq, J=18Hz, 2H), 4.76, 5.06(ABq, J=15Hz, 2H), 5.05(d, J=4.5Hz, 1H), 5.30(dd, J=4.5Hz, J=9Hz, 1H), 5.67(brs, 2H), 5.9(m, 1H), 6.21(s, 1H), 6.47(q, J=7Hz, 1H), 6.53(d, J=6.5Hz, 1H), 8.62(d, J=9Hz, 1H). | (6-2) |
| 5 | H | Me | Me | ECE | 3380, 1780, 1762, 1720, 1695, 1540. [Nujol] | 1.58(d, J=6Hz, 3H), 1.89(d, J=8Hz, 3H), 2.06(s, 3H), 2.59(d, J=6Hz, 3H), 3.62(s, 2H), 4.62, 4.91(ABq, J=14Hz, 2H), 5.22(d, J=4Hz, 1H), 5.83(s, 2H), 5.89(dd, J=4Hz, J=9Hz, 1H), 6.23(s, 1H), 6.39(q, J=8Hz, 1H), 6.95(brs, 2H), 7.12(q, J=6Hz, 1H), 9.30(d, J=9Hz, 1H). [CD$_3$SOCD$_3$] | (6-1) |
| 6 | H | Me | Me | ICE | 3440, 1778, 1750, 1675, 1542. | 1.31(d, J=6Hz, 6H), 1.56(d, J=6Hz, 3H), 1.90(d, J=8 Hz, 3H), 2.76(d, J=5Hz, 3H), 3.40, 3.59(ABq, J=19Hz, 2H), 4.80, 4.98(ABq, J=15Hz, 2H), 5.04(d, J=5Hz, 1H), 5.27(q, J=5Hz, 1H), 5.48(brs, 2H), 5.91(dd, J=5Hz, J=9Hz, 1H), 6.32(s, 1H), 6.39(q, J=8Hz, 1H), 6.71~6.74(m, 2H), 8.00(d, J=9Hz, 1H). | (6-2) |
| | | | | | (Part 3) | | |
| 7 | H | Me | Me | HCE | 3440, 3350, 1790, 1755, 1698, 1655, 1155. | 1.0~2.1(m, 10H), 1.50(d, J=6.5Hz, 3H), 2.05(d, J=8 Hz, 3H), 2.76(d, J=5Hz, 3H), 3.40, 3.61(ABq, J=18Hz, 2H), 4.3~4.7(m, 1H), 4.77, 5.07(ABq, J=15Hz, 2H), 5.02(d, J=4Hz, 1H), 5.19(dd, J=4Hz, J=8Hz, 1H), 5.30 (q, J=5Hz, 1H), 5.38(brs, 2H), 6.62(q, J=8Hz, 1H), 6.62(s, 1H), 7.98(d, J=8Hz, 1H). | (6-1) |
| 8 | H | Et | Me | AOM | 3440, 3360, 3280, 1790, 1730, 1698, 1659, 1625, 1540. [Nujol] | 1.00(t, J=7Hz, 3H), 2.07(s, 3H), 2.18(quintet, J=7Hz, 2H), 2.58(d, J=6Hz, 3H), 3.60(s, 2H), 4.60, 4.90(ABq, J=13Hz, 2H), 5.22(d, J=4Hz, 1H), 5.80(dd, J=4Hz, J=9Hz, 1H), 5.84(s, 2H), 6.22(s, 1H), 6.25(t, J=7Hz, 1H), 6.98(brs, 2H), 7.03(q, J=6Hz, 1H), 9.26(d, J=9Hz, 1H). [CD$_3$SOCD$_3$] | (6-1) |
| 9 | H | Et | Me | AOE | 1780, 1750, 1720, 1665. | 1.07(t, J=7Hz, 3H), 1.53(d, J=6Hz, 3H), 2.10(s, 3H), 2.20~2.63 (m, 2H), 2.78(d, J=5Hz, 3H), 3.33, 3.63 (ABq, J=19Hz, 2H), 4.88, 5.03(ABq, J=14Hz, 2H), 5.04(d, J=4Hz, 1H), 5.27~5.50(m, 2H), 5.91, 6.02(dd, J=4Hz, J=9Hz, 1H), 6.35(s, 1H), 6.42(t, J=7Hz, 1H), 6.90~7.28(m, 1H), 8.07(d, J=9Hz, 1H). | (6-1) |
| | | | | | (Part 4) | | |
| 10 | H | Et | Me | POM | 3410, 3330, 2970, 1780, 1745, 1715, 1660, 1620, 1525, | 1.05(t, J=8Hz, 3H), 1.22(s, 9H), 2.40(quintet, J=8 Hz, 2H), 2.77(d, J=5Hz, 3H), 3.44, 3.57(ABq, J=20Hz, 2H), 4.73~4.96(m, 1H), 4.92, 5.07(ABq, J=15Hz, 2H), | (6-1) (6-2) |

TABLE 5-continued

| | | | | | Pharmacologically acceptable ester | | |
|---|---|---|---|---|---|---|---|
| No. | R | R¹ | R² | R³ | IR(CHCl₃)ν: cm⁻¹ | NMR(CDCl₃) δ: ppm | Ex. No. |
| | | | | | 1375, 1243, 1123. [KBr] | 5.04(d, J=5Hz, 1H), 5.30(brs, 2H), 5.86, 5.93(ABq, J=6Hz, 2H), 5.95(dd, J=5Hz, J=8Hz, 1H), 6.34(s, 1H), 6.42(t, J=8Hz, 1H), 8.10(d, J=8Hz, 1H). | |
| 11 | H | Et | Me | POE | 1785, 1745sh, 1725, 1670. | 1.04(t, J=7Hz, 3H), 1.20(s, 9H), 1.54(d, J=5Hz, 3H), 2.17~2.63(m, 2H), 2.76(d, J=5Hz, 3H), 3.36, 3.63 (ABq, J=18Hz, 2H), 4.27, 5.08(ABq, J=14Hz, 2H), 5.05 (d, J=4Hz, 1H), 5.40~5.67(brm, 2H), 5.90, 6.00(dd, J=4Hz, 1H), 6.32(s, 1H), 6.41(t, J=7Hz, 1H), 6.83~ 7.20(m, 1H), 8.19(d, J=9Hz, 1H). | (6-1) |
| 12 | H | Et | Me | ECE | 1782, 1760, 1723, 1670. | 1.05(t, J=7Hz, 3H), 1.31(t, J=7Hz, 3H), 1.58(d, J=6 Hz, 3H), 2.13~2.55(m, 2H), 2.75(d, J=5Hz, 3H), 3.33, 3.60(ABq, J=18Hz, 2H), 4.22(q, J=7Hz, 2H), 4.78, 5.07(ABq, J=14Hz, 2H), 5.01(d, J=4Hz, 1H), 5.40~5.70 (br, 2H), 5.92(dd, J=4Hz, J=8Hz, 1H), 6.30(s, 1H), 6.38(t, J=7Hz, 1H), 6.75~7.10(m, 1H), 8.03~8.27(m, 1H). | (6-1) |

(Part 5)

| No. | R | R¹ | R² | R³ | IR(CHCl₃)ν: cm⁻¹ | NMR(CDCl₃) δ: ppm | Ex. No. |
|---|---|---|---|---|---|---|---|
| 13 | H | Et | Me | ICP | 3450, 1775, 1750, 1678, 1530. | 0.95(t, J=7Hz, 3H), 1.05(t, J=7Hz, 3H), 1.30(t, J=6 Hz, 6H), 1.7~2.2(m, 2H), 2.38(dq, J=8Hz, J=8Hz, 2H), 2.75(d, J=5Hz, 3H), 3.40, 3.56(ABq, J=18Hz, 2H), 4.82, 5.02(ABq, J=15Hz, 2H), 5.06(d, J=5Hz, 1H), 5.28 (q, J=5Hz, 1H), 5.42(brs, 2H), 5.92(dd, J=5Hz, J=9 Hz, 1H), 6.33(s, 1H), 6.48(t, J=8Hz, 1H), 6.72(m, 2H), 8.00(d, J=9Hz, 1H). | (6-1) |
| 14 | H | Et | Me | BCE | 3485, 3390, 1782, 1760, 1730, 1667, 1525. | 1.06(t, J=7Hz, 3H), 1.49(s, 9H), 1.56(d, J=6Hz, 3H), 2.40(dq, J=7Hz, J=8Hz, 2H), 2.76(d, J=5Hz, 3H), 3.40, 3.57(ABq, J=18Hz, 2H), 4.83, 5.03(ABq, J=15Hz, 2H), 5.03(d, J=5Hz, 1H), 5.26(q, J=5Hz, 1H), 5.32 (brs, 2H), 5.92(dd, J=5Hz, J=9Hz, 1H), 6.35(s, 2H), 6.40(t, J=8Hz, 1H), 6.90(m, 1H), 7.95(d, J=9Hz, 1H). | (4-7) |
| 15 | H | Et | Me | PeCP | 3410, 3350, 1780, 1752, 1715, 1665, 1123. | 0.94(t, J=7Hz, 6H), 1.05(t, J=8Hz, 3H), 1.22(d, J=6 Hz, 3H), 1.1~2.0(m, 6H), 2.38(quintet, J=8Hz, 2H), 2.75(d, J=5Hz, 3H), 3.41, 3.57(ABq, J=18Hz, 2H), 4.80, 4.99(ABq, J=14Hz, 2H), 4.90(m, 1H), 5.03(d, J= 5Hz, 1H), 5.28(d, J=5Hz, 1H), 5.42(brs, 2H), 5.90 (dd, J=5Hz, J=8Hz, 1H), 6.32(s, 1H), 6.47(t, J=8Hz, 1H), 7.30(m, 1H), 8.00(d, J=8Hz, 1H). | (6-1) |

(Part 6)

| No. | R | R¹ | R² | R³ | IR(CHCl₃)ν: cm⁻¹ | NMR(CDCl₃) δ: ppm | Ex. No. |
|---|---|---|---|---|---|---|---|
| 16 | H | Et | Me | DOL | 3470, 3400, 3340, 1820, 1784, 1730, 1670, 1605, 1520. | 1.02(t, J=7Hz, 3H), 2.16(s, 3H), 2.3(m, 2H), 2.73(d, J=5Hz, 3H), 3.42, 3.56(ABq, J=20Hz, 2H), 4.73, 5.08 (ABq, J=14Hz, 2H), 5.01(s, 2H), 5.03(d, J=4Hz, 1H), 5.1(m, 1H), 5.71(brs, 2H), 5.89(dd, J=4Hz, J=9Hz, 1H), 6.23(s, 1H), 6.35(t, J=7Hz, 1H), 8.43(d, J=9Hz, 1H). | (6-1) |
| 17 | H | Et | Et | POM | 3400, 3340, 2970, 1780, 1745, 1720, 1660, 1620, 1525, 1375, 1240. [KBr] | 1.05(t, J=8Hz, 3H), 1.12(t, J=7Hz, 3H), 1.22(s, 9H), 2.38(quintet, J=8Hz, 2H), 3.18(quintet, J=7Hz, 2H), 3.43, 3.52(ABq, J=18Hz, 2H), 4.93(brs, 1H), 4.78, 5.05(ABq, J=14Hz, 2H), 5.02(d, J=5Hz, 1H), 5.28(s, 2H), 5.83, 5.90(ABq, J=6Hz, 2H), 5.92(dd, J=5Hz, J=9Hz, 1H), 6.33(s, 1H), 6.40(t, J=8Hz, 1H), 8.02(d, J=9Hz, 1H). | (6-1) |
| 18 | H | Et | i-Pr | POM | 3500, 3440, 3400, 1787, 1750, 1723, 1670, 1605, 1505. | 1.03(t, J=7Hz, 3H), 1.13(d, J=7Hz, 6H), 1.28(s, 9H), 2.33(quintet, J=7Hz, 2H), 3.41, 3.55(ABq, J=17Hz, 2H), 3.7(m, 1H), 4.76, 5.06(ABq, J=14Hz, 2H), 4.83(d, J=7Hz, 1H), 5.02(d, J=4Hz, 1H), 5.51(brs, 2H), 5.84, 5.91(ABq, J=5Hz, 2H), 5.90(dd, J=4Hz, J=9Hz, 1H), 6.29(s, 1H), 6.40(t, J=7Hz, 1H), 8.28(d, J=7Hz, 1H). | (6-2) |

(Part 7)

| No. | R | R¹ | R² | R³ | IR(CHCl₃)ν: cm⁻¹ | NMR(CDCl₃) δ: ppm | Ex. No. |
|---|---|---|---|---|---|---|---|
| 19 | H | Et | i-Pr | HmCP | 3430, 3390, 1780, 1755, 1720, 1672, 1605. | 0.94(t, J=7Hz, 3H), 0.9~2.0(m, 13H), 1.03(t, J=7Hz, 3H), 1.13(d, J=7Hz, 6H), 2.33(quintet, J=7Hz, 2H), 3.41, 3.55(ABq, J=17Hz, 2H), 3.53(d, J=7Hz, 2H), 3.71(m, 1H), 4.76, 5.06(ABq, J=14Hz, 2H), 4.83(d, J= 7Hz, 1H), 5.02(d, J=4Hz, 1H), 5.51(brs, 2H), 5.90 (dd J=4Hz, J=9Hz, 1H), 6.29(s, 1H), 6.40(t, J=7Hz, 1H), 6.70(m, 1H), 8.28(d, J=7Hz, 1H). | (6-1) |
| 20 | H | n-Pr | Me | POM | 3450, 3400, 1785, 1750, 1725, 1670, 1600. | 0.92(t, J=7Hz, 3H), 1.22(s, 9H), 1.49(brq, J=7Hz, 2H), 2.35(brq, J=7Hz, 2H), 2.77(d, J=5Hz, 3H), 3.43, 3.57(ABq, J=18Hz, 2H), 4.79, 5.12(ABq, J=14Hz, 2H), 5.06(d, J=5Hz, 1H), 5.54(s, 2H), 5.84, 5.92(ABq, J=5Hz, 2H), 5.89(dd, J=5Hz, J=8Hz, 1H), 6.33(s, 1H), 6.42(t, J=7Hz, 1H), 8.14(d, J=8Hz, 1H). | (6-1) |
| 21 | H | i-Pr | Me | POM | 3450, 3390, 1785, 1745, 1720, 1670, 1600. | 1.04(d, J=7Hz, 6H), 1.20(s, 9H), 2.25(d, J=5Hz, 3H), 2.70~3.13(m, 1H), 3.42, 3.53(ABq, J=19Hz, 2H), 4.78, 5.07(ABq, J=14Hz, 2H), 5.02(d, J=5Hz, 1H), 5.29(q, J=5Hz, 1H), 5.60(brs, 2H), 5.92(dd, J=5Hz, J=8Hz, 1H), 5.98(s, 2H), 6.22(d, J=10Hz, 1H), | (6-1) |

TABLE 5-continued

| | | | | | Pharmacologically acceptable ester | | |
|---|---|---|---|---|---|---|---|
| No. | R | $R^1$ | $R^2$ | $R^3$ | IR(CHCl$_3$)$\nu$: cm$^{-1}$ | NMR(CDCl$_3$) $\delta$: ppm | Ex. No. |
| | | | | | | 6.36(s, 1H), 7.83(d, J=8Hz, 1H), | |

TABLE 6

Carboxy-deprotection

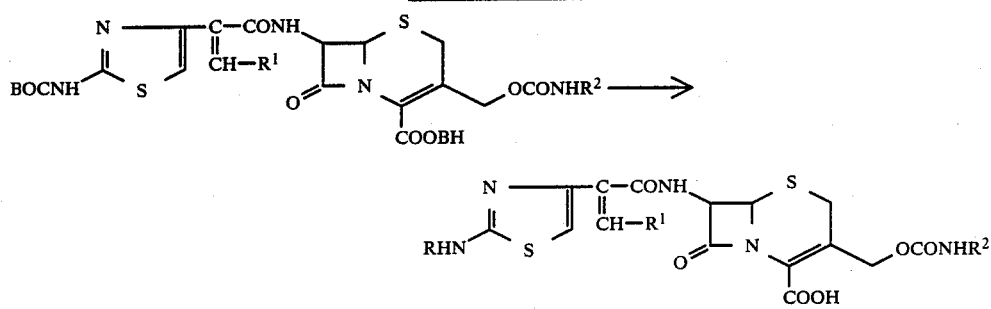

| No. | R | $R^1$ | $R^2$ | Exp. No. | S. M. (mg) | Solvent (ml) | F$_3$CCOOH (ml) | Subreagent (ml) | Time (hr) | Temp (°C.) | Yld. (%) | Crop (mg) |
|---|---|---|---|---|---|---|---|---|---|---|---|---|
| 1 | H | Me | Me | (3-1), (6-1) | 200 | — | 2.0 | anisole 0.3 | 3/2 | rt | 61 | 101 |
| 2 | H | Me trans | Me | (3-1), (6-1) | 60 | DCM 0.4 | 1.0 | anisole 2.5 | 3/2 | rt | 62 | 29 |
| 3 | H | Et | Me | (3-1), (6-1) | 40 | DCM 1.0 | 1.0 | anisole 0.5 | 5/2 | rt | 73 | 30 |
| 4 | H | Et | Et | (3-1), (6-1) | 70 | DCM 1.5 | 1.5 | anisole 0.75 | 3/2 | rt | 64 | 36 |
| 5 | BOC | Et | Et | (3-1) | 500 | DCM 5 | 1.0 | anisole 0.5 | 1/2 | 0 | 97 | 397 |
| 6 | H | Et | i-Pr | (3-1), (6-1) | 100 | — | 1.0 | anisole 0.1 | 3/2 | rt | 53 | 53 |
| 7 | H | n-Pr | Me | (3-1), (6-1) | 100 | — | 0.62 | anisole 0.2 | 1 | rt | 54 | 35 |
| 8 | BOC | n-Pr | Me | (3-1) | 1200 | DCM 5 | 5.0 | anisole 2.5 | 1 | 0 | 100 | 965 |
| 9 | H | i-Pr | Me | (3-1), (6-1) | 120 | — | 0.72 | anisole 0.25 | 1 | rt | 64 | 50 |
| 10 | BOC | i-Pr | Et | (3-1) | 442 | DCM 3 | 2.0 | anisole 1.0 | 1 | 0 | 98 | 348 |

TABLE 7

Esterification

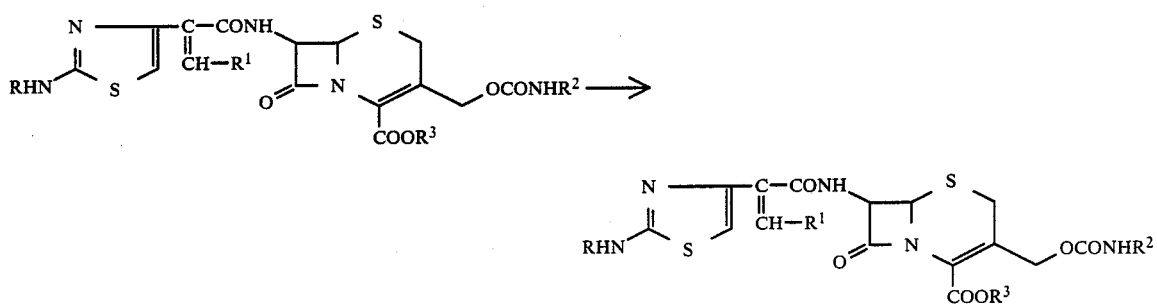

| No. | R | $R^1$ | $R^2$ | $R^3$ | $R^4$ | Exp. No. | S.M. (mg) | Solvent (ml) | Reagent (mg) | Subreagent (mg) | Time (hr) | Temp (°C.) | Yld. (%) | Crop (mg) |
|---|---|---|---|---|---|---|---|---|---|---|---|---|---|---|
| 1 | BOC | Me | Me | Na | AOM | (4-1) | 575 | DMF 3 | AOM-Br 180 | — | 1 | 0 | 45 | 281 |
| 2 | BOC | Me | Me | H | AOE | (4-2) | 553 | DMF 3 | AOE-Br 350 | Na$_2$CO$_3$ 160 | 1 | 0 | 63 | 403 |
| 3 | BOC | Me | Me | Na | POM | (4-3) | 800 | DMF 5 | POM-I 700 | — | ½ | 0 | 48 | 447 |
| 4 | BOC | Me | Me | H | HOH | (4-7) | 553 | DMA 5 | HOH-I 450 | K$_2$CO$_3$ 200 | 4/3 | 0 | 43 | 334 |
| 5 | BOC | Me | Me | H | ECE | (4-5) | 553 | DMF 3 | ECE-Br 260 | K$_2$CO$_3$ 200 | 3/2 | 0 | 63 | 422 |
| 6 | BOC | Me | Me | H | ICE | (4-7) | 553 | DMF 5 | ICE-I 330 | K$_2$CO$_3$ 200 | 4/3 | −10 | 58 | 397 |
| 7 | BOC | Me | Me | H | HCE | (4-7) | 553 | DMA 5 | HCE-I 387 | K$_2$CO$_3$ 200 | 1 | −10 | 62 | 447 |
| 8 | BOC | Et | Me | Na | AOM | (4-1) | 600 | DMF 5 | AOM-Br 200 | — | 1 | −10 | 70 | 449 |
| 9 | BOC | Et | Me | H | AOE | (4-2) | 1120 | DMF 10 | AOM-Br 650 | K$_2$CO$_3$ 325 | 3/2 | −15 | 47 | 600 |
| 10 | BOC | Et | Me | H | POM | (4-3) | 138 | DMF 1.4 | POM-I 62 | K$_2$CO$_3$ 67 | ½ | −30 | 82 | 136 |
| 11 | BOC | Et | Me | H | POE | (4-4) | 300 | DMF 3 | POE-I 250 | K$_2$CO$_3$ 110 | 4/3 | −30 | 49 | 180 |
| 12 | BOC | Et | Me | Na | ECE | (4-5) | 600 | DMF 6 | ECE-Br 260 | — | 1 | 0 | 26 | 180 |
| 13 | H | Et | Me | H | BCE | (4-7) | 467 | DMA 5 | BCE-I 360 | K$_2$CO$_3$ 200 | 4/3 | 0 | 48 | 274 |
| 14 | BOC | Et | Me | H | ICP | (4-7) | 284 | DMF 2 | ICP-I 180 | K$_2$CO$_3$ 100 | 11/6 | −10 | 61 | 218 |
| 15 | BOC | Et | Me | H | PeCP | (4-7) | 567 | DMF-5 | PeCP-I 390 | K$_2$CO$_3$ 200 | 2 | 0 | 36 | 267 |
| 16 | BOC | Et | Me | Na | DOL | (4-6) | 1000 | DMF 10 | DOL-Br 660 | — | 2 | 0 | 50 | 532 |
| 17 | BOC | Et | Et | H | POM | (4-3) | 175 | DMF 1.4 | POM-I 62 | K$_2$CO$_3$ 75 | ½ | −30 | 72 | 150 |
| 18 | BOC | Et | i-Pr | Na | POM | (4-3) | 500 | DMF 5 | POM-I 200 | — | 1 | −10 | 85 | 487 |
| 19 | BOC | Et | i-Pr | H | HmCP | (4-7) | 288 | DMF 3 | HmCP-I 215 | K$_2$CO$_3$ 100 | 3/2 | 0 | 33 | 129 |
| 20 | BOC | n-Pr | Me | H | POM | (4-3) | 233 | DMF 3 | POM-I 140 | K$_2$CO$_3$ 110 | 2 | −40 | 62 | 174 |

TABLE 7-continued
Esterification

[Reaction scheme: Starting material with RHN-thiazole, CONH, CH-R¹, β-lactam-S, OCONHR², COOR³ → Product]

| No. | R | R¹ | R² | R³ | R⁴ | Exp. No. | S.M. (mg) | Solvent (ml) | Reagent (mg) | Subreagent (mg) | Time (hr) | Temp (°C.) | Yld. (%) | Crop (mg) |
|---|---|---|---|---|---|---|---|---|---|---|---|---|---|---|
| 21 | BOC | i-Pr | Me | H | POM | (4-3) | 348 | DMF 4 | POM-I 200 | K₂CO₃ 166 | 3/2 | −35 | 68 | 282 |

TABLE 8
Carboxy-protection

[Reaction scheme: Starting material with COOH → Product with COOBH]

| No. | R | R¹ | R² | Exp. No. | S.M. (mg) | Solvent (ml) | Ph₂CN₂ (mg) | Subreagent (ml) | Time (hr) | Temp (°C.) | Yld. (%) | Crop (mg) |
|---|---|---|---|---|---|---|---|---|---|---|---|---|
| 1 | BOC | Me | Me | (4-9) | 370 | DCM 5 | 144 | MeOH 1 | 1 | rt | 41 | 200 |
| 2 | BOC | Me trans | Me | (4-9) | 100 | DCM 2 | 40 | — | ½ | rt | 61 | 80 |
| 3 | BOC | Et | Et | (4-9) | 800 | DCM 5 | 295 | MeOH 2 | 1 | rt | 75 | 770 |

TABLE 9
Carbamic esterification

[Reaction scheme: Starting material with COONa, OH → Product with COOH, OCONHR²]

| No. | R | R¹ | R² | R³ | Exp. No. | S. M. (mg) | Solvent (ml) | R²NCO (ml) | Subreagent | Time (hr) | Temp (°C.) | Yld. (%) | Crop (mg) |
|---|---|---|---|---|---|---|---|---|---|---|---|---|---|
| 1 | BOC | Me | Me | H | (5-1) | 1000 | THF 10 | 2.0 | Pyridine 1.0 ml | 3/2 | rt | 73 | 810 |
| 2 | BOC | Me trans | Me | Na | (5-1) | 130 | THF 2 | 0.074 | (n-Bu₃Sn)₂O 12 mg | 3/2 | rt | 76 | 110 |
| 3 | BOC | Et | Me | H | (5-1) | 392 | THF 4 | 0.7 | Pyridine 0.4 ml | 1 | rt | 41 | 170 |
| 4 | BOC | Et | Me | Na | (5-1) | 450 | THF 10 | 0.45 | (n-Bu₃Sn)₂O 40 mg | 3/2 | rt | 73 | 370 |
| 5 | BOC | Et | Et | H | (5-1) | 1070 | THF 10 | 1.6 | Pyridine 0.8 ml | 9/2 | rt | 75 | 870 |
| 6 | BOC | Et | i-Pr | Na | (5-1) | 1000 | THF 15 | 0.93 | (n-Bu₃Sn)₂O 95 mg | 3/2 | rt | 72 | 840 |

TABLE 10

Amino-deprotection

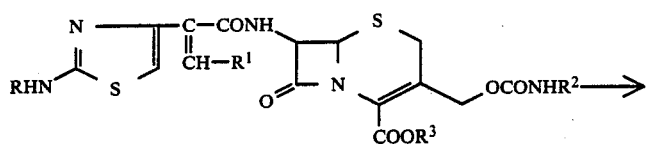

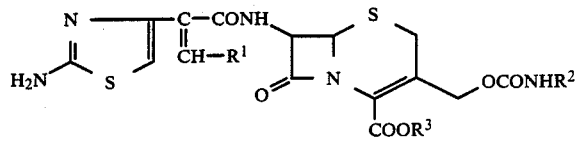

| No. | R | R¹ | R² | R³ | Exp. No. | S. M. (mg) | Solvent (ml) | Reagent (ml) | Subreagent (ml) | Time (hr) | Temp (°C.) | Yld. (%) | Crop (mg) |
|---|---|---|---|---|---|---|---|---|---|---|---|---|---|
| 1 | BOC | Me | Me | AOM | (6-1) | 250 | — | F₃CCOOH 2.0 | anisole 0.5 | 4/3 | rt | 70 | 166 |
| 2 | BOC | Me | Me | AOE | (6-1) | 320 | — | F₃CCOOH 3.2 | anisole 0.7 | 3/2 | rt | 73 | 197 |
| 3 | BOC | Me | Me | POM | (6-1) | 447 | — | F₃CCOOH 4.0 | anisole 0.3 | 1 | rt | 59 | 223 |
| 4 | BOC | Me | Me | HOH | (6-2) | 311 | DCM 1.0 | AlCl₃ 107 mg | anisole 0.5 | 1/3 | −20 | 80 | 217 |
| 5 | BOC | Me | Me | ECE | (6-1) | 335 | — | F₃CCOOH 3.5 | anisole 0.7 | 3/2 | rt | 75 | 215 |
| 6 | BOC | Me | Me | ICE | (6-2) | 342 | DCM 1.0 | AlCl₃ 110 mg | anisole 0.5 | 1/3 | −20 | 73 | 213 |
| 7 | BOC | Me | Me | HCE | (6-1) | 420 | — | F₃CCOOH 3.5 | anisole 1.0 | 5/3 | rt | 63 | 228 |
| 8 | BOC | Et | Me | AOM | (6-1) | 400 | — | F₃CCOOH 4.0 | anisole 0.5 | 1 | rt | 68 | 230 |
| 9 | BOC | Et | Me | AOE | (6-1) | 185 | — | F₃CCOOH 0.8 | anisole 0.2 | 1 | rt | 64 | 101 |
| 10 | BOC | Et | Me | POM | (6-2) | 135 | DCM 1.0 | AlCl₃ 80 mg | anisole 0.5 | 1/2 | −10 | 81 | 93 |
| 11 | BOC | Et | Me | POE | (6-1) | 170 | — | F₃CCOOH 0.8 | anisole 0.2 | 1 | rt | 49 | 72 |
| 12 | BOC | Et | Me | ECE | (6-1) | 127 | — | F₃CCOOH 0.5 | anisole 0.1 | 3/2 | rt | 59 | 64 |
| 18 | BOC | Et | Me | ICP | (6-1) | 215 | — | F₃CCOOH 1.8 | anisole 0.5 | 4/3 | rt | 49 | 91 |
| 19 | BOC | Et | Me | PeCP | (6-1) | 222 | — | F₃CCOOH 2.2 | anisole 0.5 | 4/3 | rt | 44 | 85 |
| 7 | BOC | Et | Me | DOL | (6-1) | 500 | — | F₃CCOOH 4.0 | anisole 0.5 | 1/2 | rt | 56 | 240 |
| 8 | BOC | Et | Et | POM | (6-1) | 150 | — | F₃CCOOH 2.5 | — | 1/2 | rt | 67 | 87 |
| 9 | BOC | Et | i-Pr | POM | (6-2) | 450 | DCM 3.0 | AlCl₃ 255 mg | anisole 1.0 | 1/3 | −10 | 67 | 257 |
| 20 | BOC | Et | i-Pr | HmCP | (6-1) | 125 | — | F₃CCOOH 1.5 | anisole 0.3 | 4/3 | rt | 53 | 58 |
| 10 | BOC | n-Pr | Me | POM | (6-1) | 174 | — | F₃CCOOH 1.5 | anisole 0.4 | 4/3 | rt | 43 | 65 |
| 11 | BOC | i-Pr | Me | POM | (6-1) | 282 | — | F₃CCOOH 2.5 | anisole 0.5 | 1 | rt | 60 | 145 |

TABLE 11

Reduction of Sulfoxide

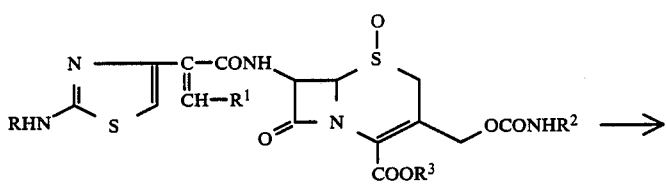

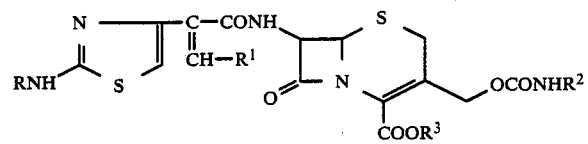

| No. | R | R¹ | R² | R³ | Exp. No. | S. M. (mg) | Solvent (ml) | Reagent (μl) | Subreagent | Time (hr) | Temp (°C.) | Yld. (%) | Crop (mg) |
|---|---|---|---|---|---|---|---|---|---|---|---|---|---|
| 1 | BOC | Et | Me | AOE | (7-1) | 187 | DCM 5 | PBr₃ 65 | — | 2/3 | −35 | 88 | 161 |
| 2 | BOC | Et | Me | ECE | (7-1) | 130 | DCM 3 | PRr₃ 44 | — | 1/2 | −35 | 100 | 127 |

TABLE 12
Sulfoxidation

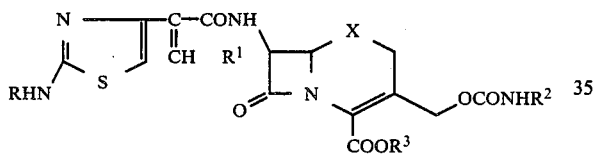

| No. | R | R¹ | R² | R³ | Exp. No. | S. M. (mg) | Solvent (ml) | Reagent (mg) | Subreagent | Time (hr) | Temp (°C.) | Yld. (%) | Crop (mg) |
|---|---|---|---|---|---|---|---|---|---|---|---|---|---|
| 1 | BOC | Et | Me | AOE | (8-1) | 600 | Chf 12 | m-CPBA 192 | — | 2/3 | 0 | 64 | 394 |
| 2 | BOC | Et | Me | ECE | (8-1) | 180 | Chf 5 | m-CPBA 60 | — | 2/3 | 0 | 70 | 130 |

What we claim is:

1. 7β-[2-(2-amino-thiazol-4-yl)-2-alkenamido]-3-(alkyl-carbamoyloxymethyl)-3-cephem-4-carboxylic acid derivative represented by the following formula:

wherein
R is hydrogen or an amino-protecting group having 1 to 19 carbon atoms and is a 1C to 8C alkyl, 7C to 19C aralkyl, 1C to 8C alkylthio, 6C to 8C arylthio, 5C to 8C cycloalkylidene, 1C to 8C alkanoyl, 2C to 8C alkoxycarbonyl, 8C to 19C aralkoxycarbonyl, 7C to 12C aroyl, 3C to 9C trialkylsilyl, 3C to 9C alkoxydialkylsilyl, 3C to 9C trialkylstannyl, 1C to 8C alkylideneamino or 7C to 12C aralkylideneamino, R¹ is 1C to 8C alkyl, R² is methyl or ethyl, R³ is acetoxymethyl, 1-(acetoxy)ethyl, 1-(cyclohexylcarbonyloxy)-1-cyclohexylmethyl, 1-(cyclohexylmethoxycarbonyloxy)propyl, 1-(cyclohexyloxycarbonyloxy)ethyl, 1-(ethoxycarbonyloxy)ethyl, 1-(isopentyloxycarbonyl-oxy)propyl, 1-(isopropoxycarbonyloxy)ethyl, 1-(isopropoxycarbonyloxy)propyl, (4-methyl-2-oxo-1,3-dioxol-5-yl)methyl, pivaloxymethyl, 1-(pivaloyloxy)ethyl, or 1-(tert-butoxycarbonyloxy)ethyl, and X is sulfur or sulfinyl.

2. The compound claimed in claim 1 wherein R is hydrogen or tert-butoxycarbonyl.

3. The compound claimed in claim 1 wherein R¹ is methyl, ethyl, propyl, or isopropyl.

4. The compound claimed in claim 1 wherein R is hydrogen and R¹ is ethyl.

5. An oral antibacterial preparation containing an antibacterially effective amount of a compound claimed in claim 1 and an inert carrier therefor.

* * * * *